United States Patent
Moore et al.

(10) Patent No.: US 8,932,715 B2
(45) Date of Patent: Jan. 13, 2015

(54) PRECIPITATION STABILISING COMPOSITIONS COMPRISING BIOACTIVE MOLECULE AND AT LEAST ONE CATIONIC AND ONE ANIONIC PRECIPITATION STABILIZING ADDITIVES

(75) Inventors: Barry Douglas Moore, Glasgow (GB); Jan Vos, Glasgow (GB); Johann Partridge, Glasgow (GB)

(73) Assignee: University of Strathclyde (GB)

( * ) Notice: Subject to any disclaimer, the term of this patent is extended or adjusted under 35 U.S.C. 154(b) by 1017 days.

(21) Appl. No.: 12/597,300

(22) PCT Filed: Apr. 25, 2008

(86) PCT No.: PCT/GB2008/001417
§ 371 (c)(1),
(2), (4) Date: Feb. 15, 2010

(87) PCT Pub. No.: WO2008/132439
PCT Pub. Date: Nov. 6, 2008

(65) Prior Publication Data
US 2010/0151247 A1    Jun. 17, 2010

(30) Foreign Application Priority Data
Apr. 25, 2007 (GB) .................................. 0707938.7

(51) Int. Cl.
*A61K 9/14* (2006.01)
*A61K 9/16* (2006.01)
*A61K 39/395* (2006.01)
*C07K 16/28* (2006.01)
*C07K 16/00* (2006.01)

(52) U.S. Cl.
CPC ............ *A61K 9/145* (2013.01); *A61K 39/39591* (2013.01); *C07K 16/00* (2013.01); *C07K 16/2818* (2013.01); *C07K 2317/21* (2013.01)

USPC .......... 428/403; 424/490; 424/491; 264/117; 264/118

(58) Field of Classification Search
CPC .................................................... A61K 9/1605
See application file for complete search history.

(56) References Cited

U.S. PATENT DOCUMENTS

| 5,324,649 A | 6/1994 | Arnold et al. |
| 5,662,883 A | 9/1997 | Bagchi et al. |

(Continued)

FOREIGN PATENT DOCUMENTS

| DE | 19925184 A1 | 11/2000 |
| EP | 1674094 A1 | 6/2006 |

(Continued)

OTHER PUBLICATIONS

Subtilisin. Sigma-Aldrich Catalog. Found online at http://www.sigmaaldrich.com/life-science/metabolomics/enzyme-explorer/analytical-enzymes/subtilisin.html.*

(Continued)

*Primary Examiner* — Holly Le
*Assistant Examiner* — Thomas Mangohig
(74) *Attorney, Agent, or Firm* — David Bradin

(57) ABSTRACT

The present invention relates to maintaining bioactive molecules in their native or substantially near-native form and preventing or reduce aggregation. In particular, the present invention relates to precipitation-protective or stabilizing additives and a method of using said precipitation-protective/stabilizing additives to protect and maintain the bioactive molecules in a native or substantially near-native form and to prevent or reduce aggregation during or following precipitation to form particles.

30 Claims, 1 Drawing Sheet

(56) References Cited

U.S. PATENT DOCUMENTS

| | | |
|---|---|---|
| 5,807,746 A | 9/1998 | Lin et al. |
| 5,945,126 A | 8/1999 | Thanoo et al. |
| 6,380,324 B1 | 4/2002 | McFadden et al. |
| 6,824,702 B1 | 11/2004 | Ohrem et al. |
| 6,825,247 B2 | 11/2004 | Ando et al. |
| 7,014,869 B2 | 3/2006 | Moore et al. |
| 7,632,799 B2 | 12/2009 | Bach et al. |
| 2002/0159954 A1 | 10/2002 | Small et al. |
| 2003/0158115 A1 | 8/2003 | Toback et al. |
| 2005/0139144 A1 | 6/2005 | Muller et al. |
| 2006/0120992 A1 | 6/2006 | Moore et al. |
| 2006/0167147 A1 | 7/2006 | Asgari |
| 2006/0292224 A1 | 12/2006 | Moore et al. |
| 2007/0026065 A1 | 2/2007 | Benke et al. |
| 2007/0196539 A1 | 8/2007 | Yang et al. |
| 2008/0286369 A1 | 11/2008 | Moore et al. |
| 2009/0226530 A1* | 9/2009 | Lassner et al. ............ 424/497 |
| 2011/0008450 A1 | 1/2011 | Moore et al. |

FOREIGN PATENT DOCUMENTS

| | | | |
|---|---|---|---|
| JP | 64-24010 A | 1/1989 | |
| WO | 9905302 A1 | 2/1999 | |
| WO | 0046147 A2 | 8/2000 | |
| WO | 0069887 A2 | 11/2000 | |
| WO | 0132125 A2 | 5/2001 | |
| WO | 0141811 A2 | 6/2001 | |
| WO | WO 2004/062560 A2 * | 7/2004 | |
| WO | WO 2006/010921 A1 * | 2/2006 | ............ A61K 9/16 |

OTHER PUBLICATIONS

Hurwitz, H., Fehrenbacher, L., Novotny, W., Cartwright, T., Hainsworth, J., Heim, W., Berlin, J., Baron, A., Griffing, S., Holmgren, E., Ferrara, N., Fyfe, G., Rogers, B., Ross, R., Kabbinavar, F. "Bevacizumab plus Irinotecan, Fluorouracil, and Leucovorin for Metastatic Colorectal Cancer." N Engl J Med 350.23 (2004): pp. 2335-2342.*

Kreiner, M., et al., "Enzyme-Coated Micro-Crystals: A 1-Step Method for High Activity Biocatalyst Preparation", "Chemical Communications", May 25, 2001, pp. 1096-1097, vol. 2001, No. 12.

Kreiner, M., et al., "DNA-Coated Microcrystals", "Chemical Communications", Apr. 20, 2005, pp. 2675-2676, vol. 2005, No. 21.

Budavari, S., et al., "An Encyclopedia of Chemicals, Drugs, and Biologicals", "The Merck Index: Twelfth Edition", Mar. 15, 1996, p. 1318 Publisher: Merck and Company.

Murdan, S., et al., "Vaccine-Coated Microcrystals: Enhanced Thermal Stability of Diphtheria Toxoid", Sep. 15-17, 2003, p. 1 British Pharmaceutical Conference 2003, Harrogate, United Kingdom.

* cited by examiner

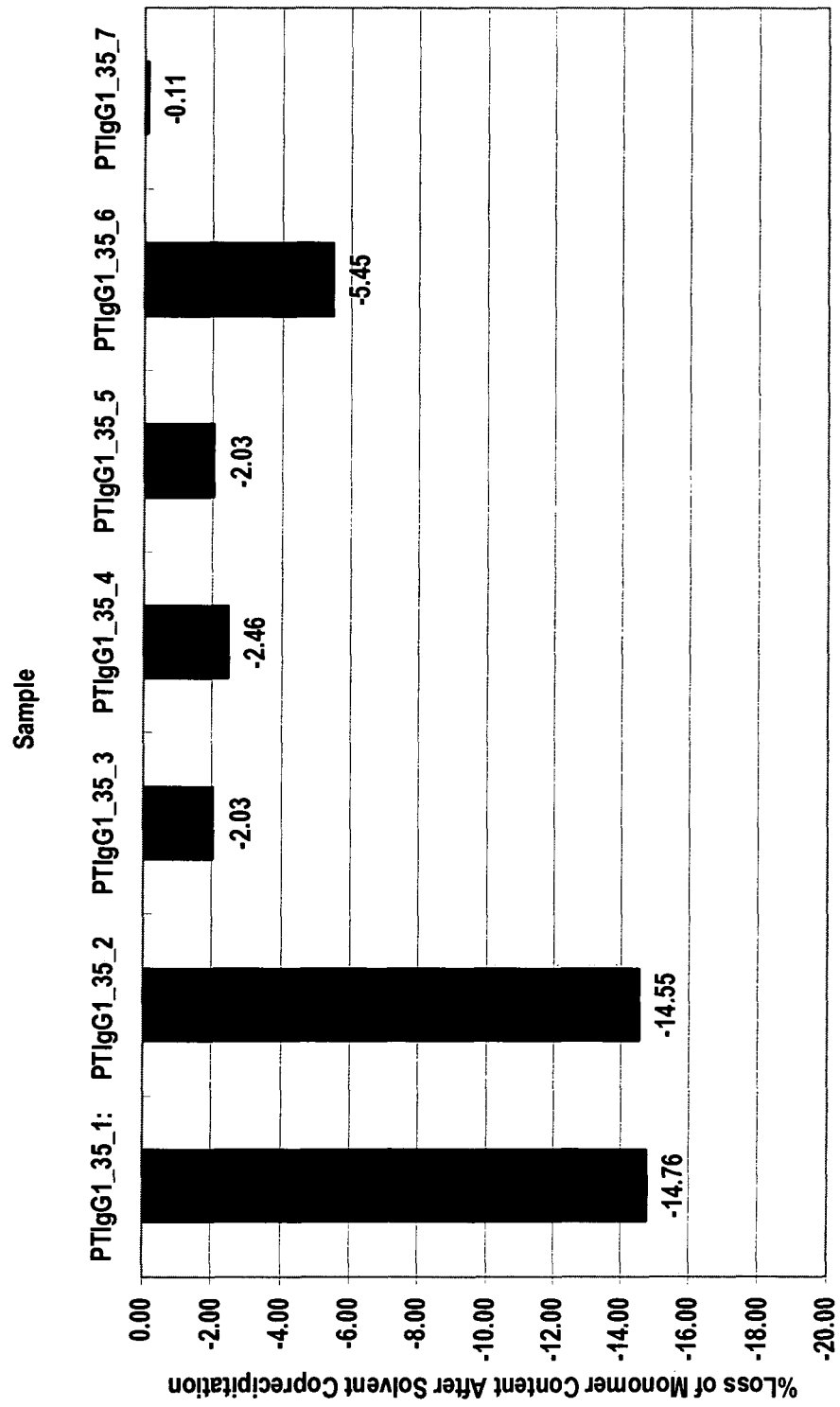

PRECIPITATION STABILISING COMPOSITIONS COMPRISING BIOACTIVE MOLECULE AND AT LEAST ONE CATIONIC AND ONE ANIONIC PRECIPITATION STABILIZING ADDITIVES

FIELD OF THE INVENTION

The present invention relates to maintaining bioactive molecules in their native or substantially near-native form and preventing or reduce aggregation. In particular, the present invention relates to precipitation-protective or stabilising additives and a method of using said precipitation-protective/stabilising additives to protect and maintain the bioactive molecules in a native or substantially near-native form and to prevent or reduce aggregation during or following precipitation to form particles.

BACKGROUND OF THE INVENTION

The retention of bioactive molecules in their native form is a key goal for formulation of conformationally sensitive therapeutic and diagnostic agents such as biomolecules. Moreover it is well-known that aggregated biomolecules can potentially cause adverse reactions following their administration.

To combat aggregation, it is well-known in the art that excipients can be introduced into a solution prior to drying by, for example, evaporative techniques such as freeze-drying or spray-drying in order to minimise the formation of aggregates. Excipients described in the art are proposed to play a number of roles including replacement of the water of hydration, inhibition of crystal formation in ice and other excipients, and as bulking agents. The most commonly used excipients during these drying processes are sugars such as trehalose and sucrose.

Another type of drying process involves precipitation of a bioactive molecule in a water miscible solvent. For, example preparation of bioactive molecule coated microcrystals may be carried out by coprecipitation into a water miscible organic solvent. This results in coating of a dehydrated bioactive molecule onto the surface of water soluble microcrystals. This is described in WO 00/69887, WO 2004/062560 and WO 2006/010921, which are incorporated herein by reference. Both exposure of the bioactive molecule to polar solvent and its immobilisation on a surface would be expected to expose it to significant stresses. Despite this in many cases the resultant dehydrated bioactive molecules are found to be present on the crystal surface in a native or near-native conformation. Also, it is commonly found that when the dry bioactive molecule coated microcrystals are admixed with a suitable aqueous buffer they dissolve to produce a visibly clear solution in which the reconstituted bioactive molecules are substantially in a bioactive state and have not, for example, formed significantly increased amounts of dimers, trimers and/or other soluble or insoluble aggregates.

However, it has now been discovered that certain bioactive biomolecules are much more adversely affected by precipitation and/or surface immobilisation processes. Precipitation can be promoted by a number of methods that reduce solubility such as changes in temperature and/or addition of polymers. Formation of bioactive molecule coated microcrystals requires a rapid simultaneous reduction in solubility of both the bioactive molecule and the crystalline core material. This is commonly achieved by rapid admixing with a large excess of a miscible non-solvent. An alternate method may involve admixing with a solution of different pH. It has been observed that when certain aggregation sensitive bioactive molecules are coprecipitated the resultant powders are found to have atypical properties. For example, on admixing the bioactive molecule coated microcrystals with aqueous buffer the resultant solution may contain light scattering particles that are visible to the eye or detectable by turbidity measurement techniques, known in the art. Alternatively, the solutions may appear optically clear but analysis by techniques such as size exclusion chromatography may show that a certain fraction of the soluble bioactive molecules have formed a different aggregation state from that existing in the solution used to prepare the coated microcrystals. For example, it may be found that the proportion of soluble bioactive molecules present as a monomer, dimer, trimer, tetramer or higher aggregate has increased or decreased relative to the proportion present before precipitation. For some applications the presence of changed levels of either insoluble or soluble aggregates following processing and reconstitution of bioactive molecule coated microcrystals may not present any problem, particularly if bioactive function is retained. However, in other important applications such as diagnostics or biopharmaceuticals significant changes in the level or type of aggregate will be unacceptable because they will alter, for example, concentration, bioavailability, bioactivity and/or immunogenicity. Bioactive molecules that may be found to present this problem include important diagnostic or therapeutic agents such as antibodies or cytokines and peptides such as hormones. There is a clear need, therefore, to find compositions and processes that enable such sensitive bioactive molecules to be formed into particles or coated onto microcrystals without significant changes to their aggregation state.

Problems of aggregation of bioactive biomolecules have been observed following application of other drying and particle-forming techniques such as freeze-drying, spray-drying and super-critical drying. It is therefore well established in the art that it can be advantageous to introduce one or more additives or excipients that help to protect a bioactive molecule during the steps required to carry out the drying process. Thus, for example, it is known in the art that certain excipients protect proteins in solution, certain excipients protect proteins, during freezing, certain excipients protect the protein during water removal steps such as sublimation or evaporation and certain excipients help stabilize the protein during storage in the dry state (Carpenter et al, Rational design of stable lyophilized protein formulations, Pharmaceutical Research, 1997, 14, 969-975). In addition it is known that certain combinations of excipients can be used to help to increase the solubility of dried proteins in aqueous solution (Duffy et al, Method to solubilize tissue plasminogen activator, U.S. Pat. No. 4,898,826; Kawahara et al, Modified tPA-containing injection composition having increased solubility, U.S. Pat. No. 5,425,943)

It should be further noted that the process for preparing bioactive molecule coated microcrystals uses no polymeric excipients whatsoever and involves simple mixing of an aqueous composition, in which the bioactive molecule and all of the low molecular weight components that form the particle are present and fully soluble, with an excess of a polar water miscible solvent. It is thus very different from processes such as complex coacervation where dispersions of protein or protein/polymer mixtures are solidified by contacting with immiscible organic solvents.

During the solvent coprecipitation process commonly used to form bioactive molecule coated microcrystals, the bioactive molecules will be exposed to a significantly different environment to that experienced in other techniques such as freeze-drying or spray-drying. In particular, the bioactive molecule solution will be mixed with high concentrations of a water miscible or partially water miscible organic solvent such as for example alcohols, ketones, esters or ethers or a mixture of these. These polar organic solvents will interact with a bioactive molecule in a very different way from air or vacuum and would for example, be expected to solvate the protein surface and displace water and other molecules present in the aqueous solution. In addition, during the precipitation process the bioactive molecule will have the potential to come into contact with a very high surface area formed by the microcrystalline carrier and the perceived wisdom is that exposure of molecules such as proteins to such surfaces should be avoided. Furthermore, following manufacture of precipitated particles such as bioactive molecule coated microcrystals at a commercial scale it may be necessary to store them in the organic solvent for periods ranging from many minutes to several hours or longer before they can be isolated and dried. This requires the identification of excipients that are able to protect bioactive molecules that are associated with precipitated particles against prolonged exposure to polar solvents. These conditions are clearly very different from those experienced by bioactive molecules during freeze-drying or spray drying. Therefore determining which excipients are likely to be appropriate for stabilising aggregation sensitive bioactive molecules during precipitation with polar solvents cannot be predicted from study of the prior art. Moreover, there is commercial interest in preparing particles of biomolecules by routes other than spray-drying, lyophilisation/milling or using supercritical fluids because these processes are capital expensive, often low yielding and expensive to run—precipitation methods using high concentrations of polar organic solvents are potentially more economic because they can be carried out rapidly, continuously and isothermally at or close to room temperature and at atmospheric pressure, using simple equipment. The bioactive molecule is simultaneously dehydrated and immobilised onto a particle during the process and water may be removed from the suspension simply by filtering and air drying.

However, common excipients used in spray-drying and lyophilisation such as sugars (e.g. trehalose) have unfortunately been found not to provide the necessary protection against aggregation of certain biomolecules when precipitation is carried out with polar organic solvents It is an object of at least one aspect of the present invention to obviate or mitigate at least one or more of the aforementioned problems.

It is a further object of the present invention to maintain dehydrated bioactive molecules in their native or substantially near-native form thereby preventing or substantially preventing changes in aggregation state.

SUMMARY OF THE INVENTION

According to a first aspect of the present invention there is provided particles comprising microcrystals, said microcrystals comprising at least one bioactive molecule wherein the particles have been prepared by precipitation of said bioactive molecule(s) from an aqueous composition comprising said bioactive molecule(s), upon contact with a polar organic solvent, wherein the aqueous composition comprises at least one cationic and/or anionic precipitation stabilising additive. In a further aspect there is provided an aqueous composition comprising a bioactive molecule and at least one precipitation-protective additive wherein the bioactive molecule and precipitation-protective additives can be coprecipitated isothermally by contacting the aqueous solution with a substantially higher volume of polar organic solvent to form particles of less than about 100 microns or less than 50 microns and thereafter said particle can be reconstituted back into aqueous form.

The precipitation protective additives may ionize, or exchange protons when exposed to an aqueous media that lies in the pH range pH 4 to pH 9. They may thus form species that are overall positively charged and cationic or overall negatively charged and anionic. Precipitation protective additives that are cationic will typically have bound one or more protons and are thereafter referred to interchangeably as either cationic precipitation protective additives or basic precipitation protective additives. These may be introduced into the precipitation mixture as salts or as neutral species. Examples of cationic or basic additives are arginine and glucosamine. Cationic additives may optionally also contain quaternary ammonium substituents.

Precipitation protective additives that are anionic will typically have released one or more protons and are thereafter referred to interchangeably as either anionic precipitation protective additives or acidic precipitation protective additives. These may be introduced into the precipitation mixture as salts or as neutral species. Examples of anionic or acidic additives are glutamic acid and glucose phosphate.

A neutral additive may also be optionally combined with either a basic or acidic additive or both to provide additional precipitation protective effects. The neutral additive may either be non-ionizable or have an overall neutral charge when exposed to a pH that lies in the range pH 4 to pH 9. Examples of neutral additives are myoinositol and asparagine.

In a preferred embodiment there is provided an aqueous composition comprising
  a) an aggregation sensitive bioactive molecule such as an antibody at a concentration e.g. 0.1 mg/ml to 100 mg/ml and optionally
  b) a coprecipitant that is neutral or has a pI in the range 4-9 such as alanine, asparagine, glutamine, glycine, histidine, mannitol, myoinositol, taurine, trehalose and valine, at a concentration less than its solubility limit and in the range 5 mg/ml to 200 mg/ml
    and if b) is present at least one precipitation protective additive(s) from c) or d) and optionally one from e) or else where b) is absent at least one from c) and at least one from d) and optionally one from e)
  c) a basic additive chosen from: amino-acids with a basic side-chain, C-protected or carboxyl-derivatised amino-acids with polar non-ionizable side-chains, and amino sugars at a concentration 0.1 mg/ml to 35 mg/ml
  d) an acidic additive chosen from: amino-acids with an acidic side-chain, N-protected or amino derivatised amino-acids with polar non-ionizable side-chains, and sugar acids (including phosphates and sulfates), at a concentration 0.1 mg/ml to 35 mg/ml
  e) a neutral non-polymeric additive selected from: neutral amino-acids with polar non-ionizable side chains, polyols, sugars, disaccharides and trisaccharides at a concentration 1 mg/ml to 50 mg/ml.

The composition may optionally be buffered with a pH buffer such as citrate, histidine or phosphate at a concentration 0.1 mM to 50 mM and pH of 4.5-8.5.

The composition may optionally further comprise a polysorbate or similar at 0.001% to 0.1% and/or an inorganic salt such as sodium chloride at less than 140 mM and preferably less than 15 mM.

Any of the amino-acids b)-e) may be present in their D- or L-form or a mixture thereof.

In a more preferred embodiment there is provided an aqueous composition comprising:
- a) an aggregation sensitive bioactive molecule such as an antibody at a concentration, e.g. 1 mg/ml to 100 mg/ml
- b) an amino-acid coprecipitant chosen from alanine, asparagine, glutamine, glycine, histidine, taurine and valine at a concentration less than its solubility limit and in the range 5 mg/ml to 200 mg/ml and at least one precipitation protective additive from c) or d) and optionally one from e)
- c) a basic amino acid such as arginine at a concentration 1 mg/ml to 35 mg/ml
- d) an acidic amino-acid such as glutamic acid at a concentration 1 mg/ml to 35 mg/ml an amino-acid different from that chosen in b) with a polar non-ionizable side-chain such as serine or citrulline at a concentration 1 mg/ml to 50 mg/ml. Alternatively rather than using an amino-acid for e) it may be preferable to use a low-molecular weight, neutral, high melting point (>150° C.) additive capable of forming multiple hydrogen bonds to the protein such as for example, the polyol, myoinositol (melting point 223-225° C.).

In a further preferred embodiment there is provided an aqueous composition for preparing particles on exposure to a comprising
- a) an aggregation sensitive bioactive molecule such as an antibody at a concentration e.g. 0.1 mg/ml to 100 mg/ml
- b) optionally but preferably a coprecipitant that is neutral or has a pI in the range 4-9 such as alanine, asparagine, glutamine, glycine, histidine, mannitol, myoinositol, taurine, trehalose and valine, at a concentration less than its solubility limit and in the range 5 mg/ml to 200 mg/ml
- c) a basic additive chosen from: amino-acids with a basic side-chain, C-protected or carboxyl-derivatised amino-acids with polar non-ionizable side-chains, and amino sugars at a concentration 0.1 mg/ml to 35 mg/ml
- d) an acidic additive chosen from: amino-acids with an acidic side-chain, N-protected or amino derivatised amino-acids with polar non-ionizable side-chains, and sugar acids (including phosphates and sulfates), at a concentration 0.1 mg/ml to 35 mg/ml
- e) a neutral non-polymeric additive selected from: neutral amino-acids with polar non-ionizable side chains, polyols, sugars, disaccharides and trisaccharides at a concentration 1 mg/ml to 50 mg/ml.

Preferably to maximise protection against changes in aggregation state of the bioactive molecule on exposure to a high concentration of polar solvent, such as >80% v/v, basic, acidic and neutral additives will all be included in the aqueous precipitation mixture along with a coprecipitant.

A particularly preferred aqueous composition comprises the bioactive molecule, an amino-acid coprecipitant such as glycine or glutamine, arginine as the basic additive, glutamic acid as the acidic additive and a further neutral additive such as asparagine, trehalose or myoinositol. The aqueous precipitation mixtures described above can be mixed with an excess of polar organic solvent to precipitate fine particles in which the initial aggregation state of the bioactive molecule is substantially retained following exposure to solvent and dehydration. Polar solvents used will typically be water miscible such as isopropanol or partially water miscible such as isobutanol. Suitable polar organic solvent should both dehydrate and precipitate the biomolecule along with associated additives and coprecipiatant. The solvent must therefore not be too polar or else additives may dissolve rather then precipitate. Typically the polar solvent will have a relative dielectric constant (relative static permittivity) at 20° C. in the range 10 to 40, more preferably the dielectric constant will be in the range 15 to 30.

Typically when the coprecipitant, b), is included the fine particles will comprise bioactive molecule coated microcrystals in which the crystalline core is made from the coprecipitant and additives c) to e) will be associated with the dehydrated bioactive molecule on the surface of the microcrystals. Thus, the composition of the particles produced will be substantially similar to the composition and ratios in the aqueous mixture in terms of the amounts of the bioactive molecule a), the coprecipitant b) and the additives c) to e). This is because the preferred precipitation protective additives are substantially solvent insoluble and will coprecipitate with the bioactive molecule and coprecipitant. Typically the loading of the bioactive molecule in particles precipitated in solvent without coprecipitant b), will be in the range 30% w/w to 70% w/w. For particles precipitated with a coprecipitant b) the loading of bioactive molecule will typically be chosen to be in the range 0.1% w/w to 50% w/w. Preferably the loading of aggregation sensitive bioactive molecule coated on the microcrystals will be in the range 1 to 45% w/w. The loading of the additives in the particle will typically be chosen to be between 1% w/w and 70% w/w. Preferably for particles containing a coprecipitant [b)] the total loading of precipitation protective additives [c)-e)] in the particle will be in the range 3 to 35% w/w. Such bioactive molecule coated microcrystals are novel and can be used directly as pharmaceutical or diagnostic formulations in the form of suspensions or dry powder or as a basis for preparing a wide variety of formulations. As dry powders they advantageously typically have higher stability towards storage at elevated temperature compared to aqueous formulations and thus can be used to prepare products which can exhibit a long shelf-life and which do not require a cold-chain for shipping or storage. Alternatively if required the dry particles may also be conveniently shipped at a temperature below zero such as −20° C. with no loss of activity. Thus, a bioactive molecule, such as an antibody coprecipitated as described may typically retain 95% to 100% of the initial monomer immediately following precipitation and following storage in a sealed vial at 40° C. for 13 weeks will typically retain >95% and preferably 97% to 100% of the initial monomer. Most preferably a coprecipitated antibody will retain 95% to 100% of the initial monomer after 26 weeks in a sealed vial at 40° C. For pharmaceutical applications it is important that the precipitated particles may be reconstituted into aqueous media to form clear solutions that contain no visible insoluble aggregates. Typically standard turbidity measurements of the reconstituted precipitated particles measured at, for example, 1 mg/ml, will give readings of less than 20 NTU, preferably less than 10 NTU, more preferably less than 6 NTU and most preferably less than 3 NTU immediately following precipitation. Typically increases of less than 10 NTU and preferably less than 6 NTU will be observed on storage at 40° C. for 13 weeks and less than 20 NTU and preferably less than 10 NTU on storage at 40° C. for 26 weeks. Most preferably reconstituted precipitated particles will give a standard turbidity reading of less than 6 NTU following storage in a sealed vial at 40° C. for 26 weeks.

In the absence of protective additives, aggregation sensitive bioactive molecules will typically show turbidity readings of greater than 20 NTU or else greater than 10 NTU immediately following precipitation with a high concentration of a polar organic solvent The turbidity reading will increase further on storage and will typically be greater than 30 NTU or else greater than 20 NTU on storage at 40° C. for 13 weeks. High levels of turbidity would typically not be acceptable in a soluble pharmaceutical formulation.

Aqueous compositions according to the present invention may be suited for use with bioactive molecules that can undergo changes in aggregation state such as any one of or combination of the following: therapeutic or diagnostic proteins and peptides; therapeutic or diagnostic nucleic acids and derivatives; carbohydrates; plasmids; viruses; viral-like particles; antigens; and derivatives and conjugates thereof. Examples of suitable proteins include: antibodies; non-antibody proteins; immunoglobulins; immunoglobulin-like proteins; non-human growth factors; enzymes; hormones; cytokines; Fc-derivatised proteins or drugs; and recombinant antigens. Examples include granulocyte-colony stimulating factor (GCSF), stem cell factor, leptin, hematopoietic factors, non-human growth factors, antiobesity factors, trophic factors, anti-inflammatory factors, receptors or soluble receptors, enzymes, variants, derivatives, or analogs of any of these proteins. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma, omega), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), erythropoietin, thrombopoietin, platelet-derived growth factor (PGDF), colony simulating growth factors (CSFs), bone morphogenetic protein (BMP), superoxide dismutase (SOD), urokinase, streptokinase, or kallikrein, receptors or soluble receptors, enzymes, variants, derivatives, or analogs of any of these proteins. Types of nucleic acids that may be aggregation sensitive include DNA, antisense DNA, RNA, antisense RNA, mRNA, siRNA.

Aggregation sensitive antibodies may be polyclonal, monoclonal, native, recombinant, human, humanized, chimeric, multispecific or single chain. Immunoglobulins from classes IgA, IgD, IgE, IgG and IgM may be used. Derivatives of antibodies may also be used and these include the antigen-binding portion produced by recombinant DNA techniques or by enzymatic or chemical cleavage of intact antibodies. Antigen-binding portions include, inter alia, Fab, Fab', F(ab').sub.2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. Antibodies that may be sensitive to aggregation on exposure to polar solvents include HERCEPTIN® (Trastuzumab), a recombinant DNA-derived humanized monoclonal antibody that selectively binds to the extracellular domain of the human epidermal growth factor receptor 2 (Her2) protooncogene; and RITUXAN® (Rituximab), a genetically engineered chimeric murine/human monoclonal antibody directed against the CD20 antigen found on the surface of normal and malignant B lymphocytes. Other exemplary antibodies include AVASTIN® (bevacizumab), BEXXAR® (Tositumomab), CAMPATH® (Alemtuzumab), ERBITUX® (Cetuximab), HUMIRA® (Adalimumab), RAPTIVA® (efalizumab), REMICADE® (Infliximab), REOPRO® (Abciximab), SIMULECT® (Basiliximab), SYNAGIS® (Palivizumab), XOLAIR® (Omalizumab), ZENAPAX® (Daclizumab), ZEVALIN® (Ibritumomab Tiuxetan), or MYLOTARG® (gemtuzamab ozogamicin), receptors or soluble receptors, enzymes, variants, derivatives, or analogs of any of these antibodies.

Analogs of naturally occurring proteins may be included such as polypeptides with modified glycosylation, polypeptides without glycosylation (unglycosylated). Derivatives of naturally occurring or analog polypeptides which have been chemically modified, for example, to attach water soluble polymers (e.g., pegylated), radionuclides, or other diagnostic or targeting or therapeutic moieties) may also be included.

Preferred aggregation sensitive bioactive molecules will typically be those with high molecular masses because these are more susceptible towards changes in aggregation state. Thus, the molecular mass of the aggregation sensitive bioactive molecule will typically be greater than 3.5 kDa to 10 KDa, preferably greater than 50 KDa and more preferably greater than 100 KDa.

Typically, the precipitation-protective additives may be in a bi-functional form and be suitable for use with pharmaceutical or diagnostic applications. They may therefore be intended to be suitable for administration to animals or humans. In particular, certain of the compositions according to the present invention are intended to be safe for systemic delivery of therapeutic biomolecules to mammals.

It is intended that the precipitation-protective additives of the present invention may, in particular embodiments, occur in pairs of precipitation-protective additives which may be added into bioactive molecule compositions to reduce or substantially reduce and/or eliminate detrimental changes in aggregation state of sensitive bioactive molecules on precipitation into water-miscible solvent and/or on storage in such a water-miscible solvent.

It is therefore intended in the present invention that, an aqueous mixture containing an aggregation sensitive biomolecule and the precipitation-protective additive, upon admixing with a water-miscible organic solvent results in the formation of a precipitate which is found to be highly soluble in aqueous solution and to exhibit minimal changes to the aggregation state of the biomolecule.

The present invention has the specific technical advantage of being capable of providing bioactive molecule coated microcrystals which are resistant to changes in aggregation state of the bioactive molecule on addition of the precipitation-protective additives and thereby allow the particles to be stored for extended periods in a solvent.

In particular embodiments, the precipitation-protective additives may be bifunctional molecules.

The bifunctional precipitation-protective molecules may comprise, for example, one functional group that may interact with the bioactive molecule more strongly than the coprecipitation solvent and a second functional group that may confer low solubility of the additive in the same coprecipitation solvent. In particular embodiments such as for proteins and peptides and derivatives thereof, the binding sites may, for example, be charged side-chains or charged terminal groups while for nucleic acids, binding sites may include phosphate groups. Hydrogen bonding sites may also be used for binding the protective additive to the bioactive molecules. Functional groups that may bind strongly to the bioactive molecule in a polar solvent include cationic groups such as protonated amines, protonated guanidines, and quaternary amines, anionic groups such as carboxylates, phosphates, sulfates and sulfonates and polar groups such as sugars and polyols.

Charged groups will typically be preferred because they are likely to bind strongly to the bioactive molecule in solvent and weakly in aqueous.

In the present invention, it has surprisingly been found that for certain bioactive molecules, such as those sensitive to aggregation on exposure to polar solvent, it is preferable to use pairs of precipitation-protective additives. Thus it may preferred to use together a cationic and anionic precipitation-protective additive, a cationic and polar precipitation-protective additive, an anionic and polar precipitation-protective additive or two different cationic, anionic or polar precipitation-protective additives. If required more than two precipitation-protective additives or pairs of additives may be used together. The precipitation-protective additives may preferably be complementary additive pairs capable of binding to different sites on the bioactive molecule. For example, one component may be capable of binding to positive side-chains and the other to negative side-chains. In such situations, the use of orthogonal binding sites will maximise the coverage of precipitation-protective additives across the exposed surface of the aggregation sensitive bioactive molecule. This may be extended further by adding a third neutral additive that can bind to non-ionic polar sites. The mole ratio of one member of the complementary additive pair to the other may be varied in the range 50:1 to 1:50 and more preferably in the range 10:1 to 1:10. This may be used to minimise the amount of each precipitation-protective additive needed to retain the bioactive molecule in its original aggregation state.

The concentration of the precipitation-protective additives in the initial mixture may be sufficient to provide a multiplicity of solvent protection molecules bound to the surface of each bioactive molecule following coprecipitation and/or drying. The concentration of the precipitation-protective additives may therefore typically be high enough to effectively compete for binding to the protein with other components present during the precipitation process. These components may include typical excipients present in the supplied protein such as buffers, salts, surfactants, antioxidants and stabilisers or chaotropic agents such as urea. One or more of these residual excipient components may be advantageously extracted into the solvent and removed or partially removed during the precipitation process.

Typically each precipitation protective additive will be present in the aqueous precipitation solution at less than 400 mM and preferably less than 100 mM. In the final precipitate the precipitation protective additives will typically make up less than 75% w/w of the solids and preferably less than 35% w/w. Generally the weight ratio of precipitation protective additives to protein in the precipitate will be less than 5:1 and preferably less than 3:1.

The part of the bifunctional precipitation-protective molecules that confers low solubility in the solvent will typically be polar and may be selected from any one of or combination of the following: zwitterionic groups such as obtained with amino-acids; groups capable of forming multiple hydrogen bonds via hydroxyls such as sugars and polyols; groups capable of forming multiple hydrogen bonds via amides such as peptides; groups capable of forming multiple hydrogen bonds via carbonyl, nitrile or nitro groups, charged groups such as cations or anions. Preferably the part of the precipitation-protective bifunctional additive that confers reduced solubility in the solvent should have a zero overall charge and will generally contribute less than 1000 Da to the overall molecular weight. Polymers and molecules containing multiple charged groups such as polycations and polyanions will not typically be preferred as precipitation protective additives because they have the potential to simultaneously bind to more than one bioactive molecule resulting in changes in aggregation state. Typically precipitation-protective additives will have a molecular mass less than 1500 Da in order to minimise the effective amount required in the solid precipitate and preferably the molecular mass will be less than 500 Da.

It is preferred that the bifunctional precipitation-protective molecules are significantly more soluble in the initial aqueous solution than in the solvent used for the precipitation. Precipitation solvents may include aqueous at a different pH or temperature, water miscible solvents and partially water miscible solvents. Preferred solvents are polar organic solvents with a relative dielectric constant between 10 and 40 such as alcohols, diols, ketones, esters and ethers and derivatives and combinations thereof that can be used for coprecipitation of bioactive molecule coated crystals. Following coprecipitation the bioactive molecule coated crystals will typically be suspended in solvent containing less than 25% v/v water and preferably less than 15% v/v water. Typically the precipitation protective additive will be at least five times less soluble in the precipitation solvent than in the initial aqueous solution and more preferably at least twenty times less soluble. Preferably the precipitation-protective additives should be suitable for incorporation into dry-powders and therefore at normal temperature and pressure they should be solids in the pure form and not liquids. Excipients such as glycerol are therefore not preferred as precipitation-protective additives. For certain bifunctional precipitation-protective additives the same type of functional group may serve as both the bioactive binding group and the group that confers low solubility in solvent.

Examples of bifunctional molecules that can be used as precipitation-protective additives include: sugar acids; polyol acids; sugar bases; polyol bases; sugar phosphates; sugar sulfonate; sugar sulfates; amino-acids with ionizable side-chains; amino-acids with polar side chains, N-protected or C-protected amino acids with polar side-chains; dipeptides; tripeptides; disaccharides; trisaccharides; vitamins and cofactors. Preferred precipitation protective additives include naturally occurring molecules and/or molecules that have been approved by the regulatory authorities such as the FDA for parenteral administration. For clarification C-protected amino-acids are derivatives in which the carboxyl group has been functionalised and is no longer acidic such as in the form of an ester (e.g. glutamine methyl ester). Further N-protected amino acids are derivatives in which the amino group has been functionalised and is no longer basic such as a N-acyl derivative (e.g. N-acetyl glutamine).

Sugar and polyol acids, sugar and polyol bases and amino-acids and derivatives are preferred precipitation protective additives. In particular embodiments these may include any or a combination of the following: galacturonic acid; galactonic acid; glucuronic acid; gluconic acid; 2-Keto-L-gulonic acid; lactobionic acid; threonic acid; mannonic acid; talonic acid; rhamnonic acid; arabonic acid; glutamic acid; aspartic acid; N-acetyl asparagine; N-acetyl glutamine; ascorbic acid; N-methyl glucamine; 1-deoxy-1-(methylamino)galactitol; N-ethyl glucamine; galactosamine; glucosamine; mannosamine; arginine; lysine; histidine; ornithine; and salts and derivatives thereof. For therapeutic and diagnostic applications naturally occurring D-sugar acids, D-sugar bases and L-amino acid and their salts and derivatives will be advantageous. In these bifunctional molecules, the ionised form of the acidic or basic group typically provides a site for electrostatically binding to the bioactive molecule such as the therapeutic protein. For the sugar acids and bases the sugar moiety minimises the solubility in the solvent, whilst for the amino-acids, the zwitterionic group minimises the solubility in the solvent.

According to a further aspect of the present invention there is provided a composition comprising:
a bioactive molecule and at least one precipitation-protective additive wherein the bioactive molecule and precipitation-protective additives can be coprecipitated by mixing with excess polar solvent to form particles of less than about 50 microns and which thereafter can be reconstituted back into aqueous form with minimal changes in aggregation state.

According to a yet further aspect of the present invention there is provided a suspension in a polar organic solvent comprising:
a bioactive molecule and at least one precipitation-protective additive wherein the bioactive molecule and precipitation-protective additives have been coprecipitated to form particles of less than about 50 microns and which thereafter can be reconstituted back into aqueous form with minimal changes in aggregation state.

According to a yet further aspect of the present invention there is provided dried particles comprising:
a bioactive molecule and at least one precipitation-protective additive wherein the bioactive molecule and precipitation-protective additives that have been coprecipitated to form particles of less than about 50 microns and which thereafter can be reconstituted back into aqueous form with minimal changes in aggregation state.

For convenience precipitation protective additives are typically prepared as a solution and a measured volume is then blended with a measured volume of a solution of the aggregation sensitive bioactive molecule, prior to precipitation to form particles. However, the precipitation mixture may be prepared by a wide variety of methods known in the art including mixing solid additive into a solution of the bioactive molecule or else mixing solid bioactive molecule into a solution of the additives. The presence of the precipitation protective additive or additives will reduce or eliminate aggregation of the bioactive molecule in the particles formed by precipitation of the aqueous mixture. Typically the precipitation will be promoted by contacting the aqueous mixture with a water miscible or partially water miscible organic solvent. Isothermal mixing of the aqueous and polar solvent will typically rapidly generate particles suspended in a precipitation mixture comprising >80% solvent. The precipitation protective additive(s) may also reduce changes in the aggregation state of the bioactive molecule on storage of the precipitated particles in the polar precipitation solvent. A precipitation protective additive is therefore advantageously included in the particle forming mixture to alleviate or prevent the aggregation of bioactive molecules exposed to high concentrations of water miscible are partially miscible organic solvents, during or following precipitation. During precipitation the precipitation protective additive(s) will also be precipitated and be included within the particle. This may be promoted by pre-saturating the precipitating solvent with the additive(s) before contacting with the aqueous mixture. Preferably substantially all of the additive or additives will precipitate and be included in the particle. In the particle the additive or additives will be coated on the surface of the coprecipitant microcrystals and will therefore be associated with or bound to the bioactive molecule. The bioactive molecule and coprecipitant will therefore typically be concentrated together in a thin layer. This is advantageous because the ratio of stabilizing additive to protein may be typically lower than is required in other types of particles. The presence of precipitation protective additive(s) will also protect the aggregation sensitive bioactive molecule within the precipitated particle against aggregation following exposure to or suspension in organic solvents, compressed gases or supercritical fluids. Stabilisation of the bioactive molecule on exposure to solvent for several minutes to hours or days may be required during concentration or delivery of a suspension of particles. Supercritical fluids such as supercritical fluid carbon-dioxide or inert compressed gases such as hydrofluorocarbons like HFC-134a may be used to remove or extract the organic solvent from a suspension of particles. Bioactive molecules within particles may also be exposed to HFC-134a or HFC-227ea when these fluids are used as propellants in delivery devices. Other excipients may also be optionally added to or be present in the precipitation mixture including pH buffers, salts, surfactants and additional stabilizers. These will typically be present at lower concentrations than the precipitation protective additive and on their own will not prevent changes in the aggregation state of the aggregation-sensitive bioactive molecule taking place during precipitation.

If it is intended to carry out a precipitation to prepare bioactive molecule coated crystals it will also be necessary to include a coprecipitant in the precipitation mixture. The role of the coprecipitant will be to form the crystalline core within the bioactive molecule coated microcrystals and it will typically be present at a higher concentration than the precipitation protective additives and at a similar or higher concentration than the bioactive molecule. In order to minimize aggregation of the bioactive molecule, maximize storage stability and provide commercially useful yields of particles, the co-precipitant should preferably be non-hygroscopic and have a solubility in pure water at room temperature in the range 20-300 mg/ml. It is also preferable for the coprecipitant to be mainly in an overall neutral form at the pH used for coprecipitation so that large quantities of buffer are not required. Preferred coprecipitants are therefore neutral or have their pI in the pH range 4-9. Thus, for example, arginine which forms hygroscopic crystals and has a high pI (10.76) and glutamic acid which has an aqueous solubility of <10 mg/ml and a low pI (3.08) will not be preferred coprecipitants. Preferred coprecipitants include zwitterions such as amino-acids, small peptides and derivatives, non-reducing sugars and polyols. General it is preferred to use precipitants that crystallize rapidly and hence they should not be polymers and have low molecular weights, typically less than 1 kDa. Particularly preferred coprecipitants are alanine, asparagine, glutamine, glycine, mannitol, myoinositol, taurine and valine. Histidine may also be used if precipitation is carried out at a pH close to its pI. If used alone coprecipitants will typically not significantly prevent aggregation of the aggregation-sensitive bioactive molecule taking place during precipitation or storage.

It will be clear to one skilled in the art that precipitating an aqueous mixture of a bioactive molecule and excipients with a 3 to 9 fold greater volume of polar solvent at room temperature, either in the presence or absence of precipitation protective additive(s), can be used to demonstrate the role of an additive(s) in preventing aggregation of the bioactive molecule. In the absence of protective additives an aggregation sensitive biomolecule will typically exhibit a 5% or greater change in aggregation state immediately following precipitation with a high concentration of polar solvent to form particles. Alternatively in the absence of protective additives an aggregation sensitive biomolecule may exhibit a greater than 5% change in aggregation state on storage in the form of dried particles at 25° C. or 40° C. for 13 weeks. A change of greater than 5% in the aggregation state of a bioactive molecule will typically not be acceptable for pharmaceutical formulations.

For many bioactive molecules, such as antibodies, changes in aggregation state can be conveniently monitored by measuring decreases in the monomer content using for example size exclusion chromatography.

Particles containing bioactive molecule coated microcrystals that include precipitation protective additives will typically redissolve into aqueous solution to form a substantially clear solution in less than 5 minutes and preferably in less than 2 minutes and most preferably in less than 30 seconds. In the absence of protective additives particles containing aggregation sensitive molecules will typically take longer to fully redissolve and may take longer than 5 minutes. Changes in the amount of insoluble aggregates following precipitation with and without additive can be conveniently monitored using turbidity measurements while changes in the amount of soluble aggregates can be conveniently monitored using size exclusion chromatography.

As exemplified, it is demonstrated the advantageous effect of including the precipitation protective additives arginine and glutamic acid when preparing particles comprising antibody-coated glycine microcrystals. However, it will be clear to one skilled in the art that the generally methodology can be applied or adapted for use with other precipitation protective additives, other particle preparations and other analytical techniques.

The solution of the additive can be made by many techniques known in the art but will typically involve dissolution of a measured mass of the additive or additives in a known volume of water or buffered aqueous solution. However, certain ionizable precipitation protective additives exhibit low solubility in deionized water when in the neutral state (e.g. glutamic acid). This makes it difficult to prepare high concentration solutions directly and the route described below may therefore be used to prepare a solution containing a pair made up of a basic precipitation protective additive and an acidic precipitation protective additive where one of the two components is poorly soluble. Use of a basic and acidic additive pair is particularly preferred because they will associate with different sites on the bioactive molecule in the solid-state and also provide pH buffering during precipitation. Typically, a solution of the most soluble protective additive component e.g. L-arginine is prepared (concentration 0.1-500 mM), such that this component is fully dissolved at a particular defined molarity. To this solution is added the required weight of the lower solubility protective additive component e.g. L-glutamic acid. Generally it is convenient to prepare an approximately equimolar ratio (concentration 0.1-500 mM) of the two components but it is not imperative to use an equimolar ratio. Indeed, it is possible to vary the ratio of an acidic precipitation protective additive to basic protective additive. However, it can be appreciated that where there is limited solubility of one of the components (e.g. L-glutamic acid), it is generally not possible to prepare solutions containing high concentrations of that component in combination with low concentrations of the other component (e.g. L-arginine). The precipitation protective additive solution is typically prepared at a higher concentration than will be used in the precipitation because it will be blended with the bioactive molecule solution leading to dilution.

Additional excipients such as pH buffer and surfactants or salts may be optionally included in the precipitation protective additive solution, typically at concentrations of less than 20 mg/ml and preferably at concentrations of less than 5 mg/ml in order to generate a solution suitable for precipitation. Preferred excipients are those known to be safe for human administration. Where the solution is to be used for preparation of bioactive molecule coated microcrystals a coprecipitant has to be added in order to form the crystalline core (e.g. glycine). The coprecipitant will typically be added at higher concentrations (20-300 mg/ml) than the above excipients with the amount required depending on the aqueous solubility of the coprecipitant. The coprecipitant will typically be added to or mixed with the precipitation protective additive solution so it is present at 10 to 90% of its room temperature saturated aqueous concentration. This means that typically the coprecipitant concentration in the additive solution will be higher for a high solubility coprecipitant such as glycine (e.g. 150 mg/ml) than for a low solubility coprecipitant such as glutamine (e.g. 25 mg/ml)

Once any additional excipients have been dissolved in the protective additive solution, the pH may optionally be set to a required value, typically chosen so that the bioactive molecule of interest will have high stability in the solution and/or once precipitated. The pH is conveniently set, using a low volume of a high concentration (typically 1 M) acid (e.g. HCl) or base (e.g. NaOH)), to ensure that the concentrations of the additives and excipients (e.g. L-arginine, L-glutamic acid and glycine) are not significantly altered. Typically the pH will be in the range pH 3-pH 8. Preferably the pH will be chosen to obtain high stability on storage of the bioactive molecule in the solid state at elevated temperature.

A predefined amount of bioactive molecule may then be mixed with the buffered additive and excipients to form the final precipitation solution. By varying the amount of bioactive molecule its theoretical protein loading (TPL) and subsequently its measured protein loading (MPL) within each particle can be varied as required. Thus it is possible to make very low loadings or very high loadings depending on the strength of dose required. The bioactive molecule may be provided as a solid powder, suspension or solution. A solution is preferred so that mixing can be carried out with minimal energy input. The bioactive molecule may also contain low levels of residual excipients including pH buffers such as citrate phosphate or histidine, salts such as sodium chloride, surfactants such as polysorbate, antioxidants and other excipients known in the art. These excipients may be diluted or further removed by dialysis if necessary. In the absence of the protective additive(s) these residual excipients will typically not protect the bioactive molecule against aggregation during precipitation. However, they may provide synergistic effects in combination with the protective additives. On mixing with the precipitation solution a clear aqueous solution of the bioactive molecule in its native or required aggregation state will preferably be produced. The bioactive molecule will generally be present at a concentration of 0.01 mg/ml to 100 mg/ml in this final precipitation solution and preferably at a concentration of 0.1 mg/ml to 70 mg/ml. The protective additives will generally be present at a mass concentration of between 0.01 and 50 times the concentration of the bioactive molecule and preferably at a mass concentration of between 0.1 and 5 times that of the bioactive molecule. When the final precipitation solution is to be used to prepare bioactive molecule coated microcrystals a coprecipitant must also be present in the final precipitation solution. The coprecipitant is generally present at a mass concentration of between 1 and 1000 times that of the bioactive molecule and at between 10 and 90% of its aqueous saturation concentration. Because the coprecipitant and additives will all coprecipitate the composition of the precipitated particles can be predicted from the amounts present in the aqueous precipitation mixture. Typically the measured protein loading (MPL) will be very similar to the theoretical protein loading (TPL) which shows that all of the solid components in the aqueous precipitation mixtures are incorporated into the particles. Preferably the MPL will be within 90-110% of the TPL. The skilled reader will appreciate that the composition of the precipitation solution should therefore be chosen according to the required loading of the particles and the solubility of the coprecipitant. Thus, for particles of a specific loading, higher concentrations of the bioactive molecule and precipitation protective additives will typically be required when using coprecipitants with high aqueous solubility than when using coprecipitants with low aqueous solubility. Similarly if a particular coprecipitant and or additive(s) concentration is used the loading of the bioactive molecule in the final particles can be increased by increasing its concentration in the precipitation mixture.

Precipitation of particles from the final solution is typically carried out by mixing it with a suitable quantity of a water miscible organic solvent such that formation of particles takes place. This may be carried out at any temperature below the denaturation temperature of the bioactive molecule in the aqueous solution but is typically carried out at a temperature in the range 1-50° C. and preferably in the range 4-40° C. In order to form bioactive molecule coated microcrystals the aqueous mixture is generally added to a large excess of the precipitating solvent. Bioactive molecule coated microcrystals may be typically be prepared by mixing the final precipitation mixture with a greater than 3 fold excess of a water miscible solvent and preferably a greater than 5 fold excess of solvent. The mixing may be carried out as a batch process or as a continuous process and leads directly to the formation of bioactive molecule coated microcrystals via coprecipitation of the solvent insoluble components (see previous patents). A batch process is useful for laboratory testing of samples while a continuous process, in which the solvent and aqueous mixtures are continuously pumped into a dynamic or static mixer, will be more appropriate for manufacturing of commercial product or clinical supplies. In either type of process the precipitation protective additives are able to alleviate or prevent changes in the aggregation state of the bioactive molecule arising within the resultant particles. Intensive mixing of the aqueous and excess solvent stream can be used to precipitate particles, typically with a laser diffraction determined diameter of less than 100 microns, and preferably with a diameter of less than 50 microns or less than 10 microns and with a narrow size-distribution. Typically more polar solvents such as isopropanol can be used to obtain smaller particle sizes than less polar solvents such as isobutanol, when using similar mixing conditions but polar solvents also tend to be most damaging to aggregation sensitive bioactive molecules. Thus, precipitation protective additives are particularly advantageous for preparing particles with a diameter of less than 20 microns and preferably less than 10 microns where the particles comprise aggregation sensitive bioactive molecules. On preparation the particles initially form a suspension in the solvent which can either be filtered immediately or concentrated by techniques known in the art such as centrifugation or cross-flow filtration or hollow-fibre based concentration. The concentration process steps require the bioactive molecules on the particles to be exposed to the solvent for longer periods, typically 0.1-2 hours and possibly as long as 2-48 hours. During these procedures the precipitation protective additives alleviate or prevent changes in the aggregation state of bioactive molecules within the particles. Concentration will typically increase the solids content of the particle suspension in the solvent from about 0.1-0.5% w/v to 2.5-15% w/w.

The simplest route to isolate the particles is by filtration using a membrane filter followed by air-drying at 25° C. for 1 to 16 hours. On a small scale, filtration can be carried out rapidly but it becomes a much more difficult process to operate at larger scale. An alternate method is to concentrate the particles and then extract the remaining solvent by supercritical fluid drying. This has the advantage of preventing or minimizing compaction of the particles into a cake and typically leaves them as a free-flowing or loosely divided powder in the extraction container. It has been found that the presence of the precipitation protective additives within the particles is advantageous because they minimise or prevent changes to the aggregation state of the bioactive molecule taking place during the extraction of the water miscible solvent from the particles with supercritical carbon dioxide. Thus, the additives are able to stabilize the aggregation sensitive biomolecule during exposure to the polar organic solvent, during exposure to the supercritical fluid and during exposure to mixtures of them both.

BRIEF DESCRIPTION OF THE DRAWINGS

Embodiments of the present invention will now be described, by way of example, with reference to the accompanying drawings in which:

FIG. 1 is a representation of a variety of buffer systems according to the present invention vs. percentage loss of monomer content after solvent coprecipitation. PTIgG1_35_1=No Additive, no pH control (Example 1a); PTIgG1_35_2=No Additive, with pH control (Example 1b); PTIgG1_35_3=Gluconic acid/Sodium Gluconate (Example 1c); PTIgG1_35_4=Gluconic acid/Methyl-D-glucamine (Example 1d); PTIgG1_35_5=Sodium Glutamate (Example 1e); PTIgG1_35_6=L-Aspartic Acid Sodium salt (Example 1f); PTIgG1_35_7=L-Arginine/L-Glutamic Acid HCl (Example 1g); The monomer content of the IgG stock=93.5%.

DETAILED DESCRIPTION

The present invention relates to precipitation-protective additives and, in particular, pairs of precipitation-protective additives that may be added into bioactive molecule compositions to significantly reduce or eliminate detrimental changes in aggregation state of sensitive bioactive molecules on precipitation into water-miscible solvent and/or on storage in the solvent. Thus, if an aqueous mixture containing an aggregation sensitive biomolecule and at least one precipitation-protective additive is admixed with a water-miscible organic solvent the resultant precipitate is found to be highly soluble in aqueous solution and to exhibit minimal changes to the aggregation state of the biomolecule. This is of significant advantage for therapeutic and diagnostic applications where for example, bioactive molecule coated microcrystals can be used for delivery of effective amounts of therapeutic or diagnostic agents or antigens. The ability to store the particles for extended periods in the solvent is of particular benefit for large scale-manufacture because it may not be possible or convenient to separate or dry them from the solvent immediately following precipitation.

Suitable precipitation-protective additives are bifunctional molecules. These bifunctional precipitation-protective molecules generally contain one functional group that interacts with the bioactive molecule more strongly than the coprecipitation solvent and a second functional group that confers low solubility of the additive in the same coprecipitation solvent. For proteins and peptides and derivatives thereof binding sites may, for example, be charged side-chains or charged terminal groups while for nucleic acids binding sites may include phosphate groups. Hydrogen bonding sites may also be used for binding the protective additive to the bioactive molecule.

It has surprisingly been discovered that for aggregation sensitive bioactive molecule it is preferable to use pairs of precipitation-protective additives. Preferred are complementary additive pairs capable of binding to different sites on the surface. For example, one component may be capable of binding to positive side-chains and the other to negative side-chains. This will maximise the coverage of precipitation-protective additives across the exposed surface of the aggregation sensitive bioactive molecule. The use of electrostatic interactions for binding of the precipitation-protective additives can be advantageous because the binding will become stronger as the dielectric constant of the solvent is reduced during the coprecipitation process.

The concentration of additive included may be sufficient to provide a multiplicity of solvent protective molecules bound to the surface of each bioactive biomolecule following coprecipitation and or drying. The concentration of the precipitation-protective additives therefore needs to be high enough to effectively compete for binding to the protein with other components present during the precipitation process.

Suitable functional groups for imparting low solubility in the coprecipitation solvent include zwitterionic groups such as obtained with amino-acids and functional groups containing multiple hydroxyl groups such as sugars and polyols. These groups should preferably be well solvated by water but be poorly solvated in solvents such as alcohols, ketones, esters and ethers used for coprecipitation to form bioactive molecule coated microcrystals. Thus, surprisingly ionic and non-ionic surfactants which have significant non-polar character are not generally suitable as precipitation protective additives although they are commonly used in aqueous formulations of aggregation sensitive bioactive biomolecules. For certain bifunctional precipitation-protective additive molecules the same type of functional groups may serve as both the protein binding group and the solvent insoluble group. Thus, certain disaccharides such as trehalose may bind to the protein via hydrogen bonding and also be insoluble in the polar coprecipitation solvent. These types of additives are not generally preferred because hydrogen bonding can be disrupted by protic solvents. In addition such additives will tend to be randomly bound across the bioactive molecule surface and not be located at specific sites as can be obtained for precipitation-protective additives that bind via electrostatic interactions. This makes it more difficult to obtain an optimal formulation.

Polyionic molecules such a phosphate are another example of bifunctional precipitation-protective additive molecules where the same type of functional group may serve as both the protein binding group and the solvent insoluble group. Thus these molecules can bind electrostatically to the bioactive molecule via one charged group and have limited solubility in the solvent because of poor solvation of the remaining charged groups. Generally such additives will not be preferred because of the possibility of simultaneously electrostatically binding to two different bioactive biomolecules. This type of bridging interaction may lead to detrimental changes in the aggregation state of the bioactive molecule on reconstitution of the precipitate into aqueous solution.

Effective precipitation-protective additives include sugar acids and sugar bases. In these bifunctional molecules the acidic or basic group provides a site for electrostatically binding to the bioactive molecule and the sugar moiety minimises the solubility in the solvent. Sugar acids are generally able to cyclise quite rapidly to form lactones and in this form they are likely to be less effective as precipitation-protective additives because they can no longer bind electrostatically. Examples of effective sugar acids and sugar bases include galacturonic acid; galactonic acid; glucuronic acid; gluconic acid; 2-Keto-L-gulonic acid; lactobionic acid; threonic acid; mannonic acid; talonic acid; rhamnonic acid; arabonic acid; N-methyl glucamine; 1-deoxy-1-(methylamino)galactitol; N-ethyl glucamine; galactosamine; glucosamine; mannosamine and salts and derivatives thereof. Additives advantageous for therapeutic and diagnostic applications are those already present in vivo or those that have been shown to be safe for administration. Another preferred class of precipitation-protective additives are amino-acids with acidic or basic side-chains. These bifunctional additives can electrostatically bind to the bioactive molecule in the precipitation solvent and exhibit limited solubility because of the poor solvation of the remaining zwitterionic group. Examples include glutamic acid, aspartic acid, histidine, lysine and arginine. L-amino-acids are particularly advantageous for therapeutic and diagnostic applications because they are already present in vivo but other forms may also be safe for administration. Another preferred class of precipitation-protective additives are N- or C-protected amino-acids that have non-ionizable polar side-chains and derivatives and salts thereof. In these bifunctional molecules the unprotected amine or carboxylic group provides a site for electrostatic binding to a bioactive molecule and the polar side-chain minimises the solubility in solvent.

In general preferred bifunctional precipitation-protective additives will be those which can be administered with no detrimental physiological effects at the concentrations present in an effective dose of the bioactive molecule.

One object of this invention is therefore to provide compositions containing one or more precipitation-protective additives and a bioactive molecule that can be precipitated to form particles from which the bioactive biomolecule can be recovered in a substantially similar aggregation state to that of the aqueous solution used in the precipitation process. Such compositions should be suited for use with aggregation-sensitive bioactive molecules such as, for example, antibodies, hormones, antigens and cytokines. Preferably the bifunctional additive(s) should also be suitable for pharmaceutical or diagnostic applications and so should be safe to be administered to animals or humans. Most preferably the compositions should be safe for systemic delivery of therapeutic biomolecules to mammals.

A second object of this invention is to provide compositions containing one or more precipitation-protective additives, a bioactive molecule and a coprecipitant that can be coprecipitated to form particles from which the bioactive molecules can be recovered in a substantially similar aggregation state to that of the initial aqueous solution. Preferred compositions are those that can be used to produce particles in the form of water soluble microcrystals coated with the bioactive molecule. Such compositions should also be preferably suited for use with aggregation-sensitive bioactive molecules such as, for example therapeutic proteins including antibodies, hormones, antigens and cytokines.

A third object of this invention is to provide a suspension of particles in a solvent that comprise a bioactive molecule and one or more precipitation-protective additives that may, either as a suspension or following drying, be reconstituted in aqueous solvent to produce solutions in which the bioactive molecule is substantially in the aggregation state present prior to particle formation. The solvent may be a pure solvent or mixture of solvents and will typically be a polar water miscible organic solvent. If required the particles may also be suspended in a compressed gas or a supercritical fluid. Preferably the suspension of particles in solvent may be stored for between 1-5 hours, more preferably between 5-24 hours and most preferably between 24-168 hours with no substantial change in the aggregation state of the bioactive molecule. Thus, preferably less than 10% of bioactive biomolecules should exhibit a change in aggregation state more preferably less than 5% even more preferably less than 2% and most preferably less than 0.5%. If necessary the temperature of the solvent during storage may be controlled in the range −70 to +37 C. or preferably +4 to +25 C. The particles may have maximum cross-sections in the range 0.01-100 microns and preferably in the range 0.05-20 microns. Optionally the particles may be suspended in other solvents hydrofluorocarbons. Preferably the particles are in the form of bioactive molecule coated microcrystals or agglomerates of bioactive molecule coated microcrystals.

A fourth object of this invention is to provide dry particles comprising a bioactive molecule and one or more precipitation-protective additives that may be reconstituted in aqueous solvent to produce solutions in which the bioactive molecule is substantially in the aggregation state present prior to particle formation. Preferably the particles are in the form of bioactive molecule coated microcrystals. Such particles should preferably be suitable for storage at 25 C. for periods greater than 3 months, more preferably greater than 1 year and most preferably for greater than 2 years with no substantial change in the aggregation state of the bioactive molecule. Thus, preferably less than 10% of bioactive biomolecules exhibit a change in aggregation state, more preferably less than 5%, even more preferably less than 2% and most preferably less than 0.5%.

Whilst specific embodiments of the invention have been described above, it will appreciated that departures from the described embodiments may still fall within the scope of the invention. For example, any suitable type of precipitation-protective additive may be used to prevent or substantially prevent aggregation of the bioactive molecule.

EXAMPLES

Example 1

FIG. 1 represents a variety of buffer systems vs. percentage loss of monomer content after solvent coprecipitation.

Details of the conducted experiments and the preparation and the analyzing of the IgG PCMCs are shown below.

1.1: Calculations of Loading

The concentration of protein in stock solution was ascertained using UV absorbance measurements. Protein loading was defined as weight, ratio of protein solution to coprecipitant solution e.g. 0.8 ml of 10 mg/ml IgG solution to 1.2 mL of 50 mg/ml DL-valine solution=8 mg IgG to 60 mg of DL-valine=11.8% w/w IgG loading. The loading can be determined more precisely by also including the weight of the precipitation-protective additives into the final solids weight. This usually accounts for approximately 5-20% w/w. The aqueous to solvent ratio was defined as a volume percent e.g. a 2 mL protein, precipitation-protective additive and coprecipitant solution added to 40 mL of solvent=4.8% v/v.

1.2: Preparation of Solvent Vessel

Batch coprecipitations were typically carried out in a 125 mL glass powder round vial. The required volume of solvent, (e.g. 40 mL isopropanol, IPA) was measured out and transferred into this vessel, along with a 40 mm stirrer bar. The bottle was placed on a magnetic stirrer unit and the solvent stirred at the maximum speed (e.g. 1500 rpm). It is important to ensure that the mixing in the vessel is effective to ensure rapid coprecipitation of PCMC. For preparation of larger quantities of material the same formulations and ratios of aqueous to solvent may be used in a continuous precipitation process.

1.3: Preparation of Protein Coprecipitant/Precipitation Protective Additive/Solution Typically solutions of precipitation-protective reagent 1 (e.g. L-arginine) and where required precipitation-protective reagent 2 (e.g. L-glutamic acid) were prepared in deionised water (e.g. 50-200 mM). These were optionally mixed to give the required pH solution (e.g. pH 7.4) by for example taking the component nearest the target pH and adding sufficient of the other component to reach this value. Alternatively the pH of the mixture may be set by addition of concentrated acid, base or buffer to a pre-formed mixture. Sufficient coprecipitant was added to make the required concentration (e.g. DL-valine 50 mg/ml). and the solution mixed with a pre-defined volume of stock protein solution (e.g. Bovine IgG @ 10 mg/ml), to give the desired protein loading, e.g. 0.8 ml of stock bovine IgG solution with 1.2 ml of DL-valine coprecipiatant/solution.

1.4: Coprecipitation

The protein/coprecipitant/precipitation protective additive blend was typically added to the solvent using a 1 mL pipette in a dropwise fashion. The solvent solution should normally turn cloudy almost immediately on addition of solution to solvent, to form a white suspension. The suspension was typically mixed for 1 minute to ensure that the coprecipitation process was complete. Thereafter the PCMC product was collected.

1.5: Drying

The crystals were typically harvested from suspension by filtering on a tarred 0.45 μm Millipore Durapore membrane filter. The collected crystals were typically air dried for approximately 12-24 hours at room temperature. After drying, the crystals were removed from the filter membrane and stored in a sealed vial at room temperature.

1.6: Analysis

In order to assess each IgG PCMC formulation the following analyses were carried out.

The net weight of crystals harvested from suspension was recorded to ascertain crystal recovery. A known weight (e.g. 12.5 mg) of PCMC crystals were dissolved into 1.5 ml of PBS buffer (pH 7.4) to give a nominal concentration of ~1 mg/ml. The reconstitution profile was assessed visually to determine the clarity of the solution. (0=equivalent to buffer, 5-heavily aggregated). The solution was filtered through a 0.45 um syringe filter to ensure exclusion of any insoluble protein aggregates and the UV absorbance measured at 280 nm to quantify protein concentration, relative to a standard curve. The monomer content within the filtered solution was determined by size exclusion chromatography by injecting 20 μl of the solution of ~1 mg/ml nominal IgG concentration on a Tosoh TSKGel G3000 and G2000 SWXL, 7.8×300 mm column run in series. The separation was typically performed using 200 mM phosphate pH 7.0 buffer, at 0.7 mL/min, 25° C., with a run time of ~40 min and protein detected at 214 nm. SDS-PAGE gels were also typically measured and showed that no cleavage takes place during the process.

Results
IgG-Valine PCMC

TABLE 1

Effect of solvent protective aditives

| Sample | Ion Pair Additive | Excipient/ solvent | Theoretical Protein Loading (% w/w) | % w/w of Ion Pair Additive | Recon Profile | Monomer Content (%)* | Soluble Protein Recovery (%)** |
|---|---|---|---|---|---|---|---|
| PTIgG1 | None | DL-Valine/ IPA | 11.76 | 0.0 | 2 | 64.15 | 88 |
| PTIgG1 | Gluconic acid/ N-methyl glucamine | DL-Valine/ IPA | 9.14 | 22.3 | 1 | 84.70 | 98 |
| PTIgG1 | L-glutamic Acid/ L-arginine | DL-Valine/ IPA | 9.52 | 19.1 | 1 | 85.56 | 97 |

*Stock IgG solution = 92% monomer
**Based on (protein recovered)/(protein in) * 100

From the results shown in Table 1 it is clear that the solvent protective additives inhibit the formation of aggregates when the IgG is exposed to a polar solvent. Without the solvent protective additives, IgG coprecipitated into IPA to form IgG-valine PCMC is very susceptible to aggregation, resulting in a cloudy solution with approximately 10% of protein insoluble in the reconstitution buffer. There is also significant reduction in the monomer content of the soluble protein. In contrast when using the ion pair reagents, close to 100% of protein is recovered on reconstitution and a significantly higher proportion of IgG is retained as monomers. Clearly, using solvent-protective additives protects the IgG molecule from aggregation.

Example 2

In order to make a comparison with other known excipients a range of myo-inositol PCMC were made with these present during coprecipitation. Myo-inositol was chosen as the coprecipitant because it does not have any buffering capacity and so pH can be controlled by the residual buffer in the IgG stock solution. IgG-Glycine PCMC were also prepared with the glutamic acid-arginine solvent protective additive pair Methods The preparation method and analysis procedures were as used in Example 1 with the substitution of myo-inositol or glycine for the valine coprecipitant.

Results

From the results it can be seen that commonly used sugar and surfactant excipients such as sucrose, mannitol, trehalose and Tween 80 do not offer the same protection against changes in the soluble monomer content as the solvent protective additives. Tween 80, normally used as a low concentration excipient to inhibit IgG aggregation does not offer the same protection in PCMC coprecipitation, and results in a significant loss in monomer content. Sucrose, although capable of slightly improving monomer relative to the control, leads to a very poor reconstitution profile. For mannitol, again there is a further loss in the monomer content and for trehalose the material could not be recovered. The best retention of monomer content was obtained with the solvent protective additive pair gluconic acid/N-methyl glucamine where >95% of the original monomer content was retained. Similar results were obtained with L-glutamic acid/L-arginine when used in the preparation of the IgG-glycine PCMC.

Example 3

Other solvent protective additives were tested and the difference between using a single additive and a complementary pair was assessed using D,L-valine as the carrier and IPA as the water miscible solvent.

Methods

The preparation method and analysis procedures were as used in Example 1. IPA was obtained from BDH

TABLE 2

Comparison with other excipients

| Sample | Ion Pair Additive | Excipient | Theoretical Protein Loading (% w/w) | % w/w of Ion Pair Additive | Recon Profile | Monomer Content† (%) | Delta monomer (%) |
|---|---|---|---|---|---|---|---|
| PTIgG1_45_1 | None | Myo-inositiol | 11.1 | 0 | 2 | 78.5 | −13.5 |
| PTIgG1_45_3 | Gluconic acid/ N-methyl glucamine | Myo-inositiol | 10.0 | 9.8 | 2 | 87.4 | −4.6 |
| PTIgG1_45_4 | Tween 80 | Myo-inositiol | 11.1 | 0.2 | 1 | 72.5 | −19.5 |
| PTIgG1_45_5 | Sucrose | Myo-inositiol | 9.34 | 16.0 | 4 | 82.8 | −9.2 |
| PTIgG1_45_7 | Mannitol | Myo-inositiol | 10.0 | 9.2 | 2 | 76.7 | −15.3 |
| PTIgG1_45_10 | Trehalose | Myo-innositol | * | * | 5 | * | * |
| PTIgG1_45_10 | L-glutamic acid/ L-arginine | glycine | 9.51 | 19.2 | 1 | 87.2 | −4.8 |

† Stock IgG solution = 92% monomer
* Product could not be recovered

Results

TABLE 3

Other solvent protective additives

| Sample | Conditions | Monomer Content (%)[†] | Recon |
| --- | --- | --- | --- |
| PTIgG1_35_1 | No buffer, no pH control | 79.7 | 1 |
| PTIgG1_35_2 | No buffer, with pH control | 79.9 | 1 |
| PTIgG1_35_3 | Gluconic acid/sodium gluconate | 91.6 | 1 |
| PTIgG1_35_4 | Gluconic acid/methyl-D-glucamine | 91.2 | 1 |
| PTIgG1_35_5 | Sodium glutamate | 91.6 | 1 |
| PTIgG1_35_6 | L-aspartic acid Na salt | 88.4 | 1 |
| PTIgG1_35_7 | L-arginine/L-glutamic acid HCl | 93.4 | 1 |

[†]Stock IgG solution = 93.5% monomer

The change in the monomer content following coprecipitation and reconstitution is plotted on FIG. 1. Clearly in all cases the solvent protective additives significantly reduce the change in aggregation state of the IgG antibody. The L-arginine/L-glutamic acid:HCl pair show a less than 0.2% increase. These physiologically acceptable solvent protective additives could therefore be beneficially used for preparing therapeutic biomolecules (e.g. human or humanized monoclonal antibodies) in particulate form either as suspensions in solvent or as dry powders. Particulate preparations are of particular benefit because they can provide a route for developing alternate delivery routes for administering therapeutic biomolecules.

Example 4

Comparison of Human Monoclonal Antibody Coated Glycine Microcrystals Prepared with and Without Precipitation Protective Additives Definitions Used in this and Examples 4-15

TPL—Theoretical Protein Loading
Definition: Estimation of anticipated protein loading after aqueous protein/coprecipitant/protective additive solution has been added to the solvent
Units: % w/w $$\text{Calculations } \frac{\text{Weight of Protein Added (mg)}}{\text{(Total Solids Added) } TSA \text{ (mg)}} \times 100$$

MPC—Measured Protein Concentration
Definition: Measured protein concentration, as deduced by analytical method (UV or HPSEC)
Units: mg/ml
Calculations: None—Extrapolation from standard curve of calculated from extinction coefficient
AXC—Analytical Xstal Concentration
Definition: Recorded weight of PCMC crystals dissolved in recorded volume of diluent when reconstituting.
Units: mg/ml $$\text{Calculations } \frac{\text{Weight of Crystals (mg)}}{\text{Volume of Diluent (ml)}}$$

MPL—Measured Protein Loading
Definition: Accurate measured loading of protein payload on crystals prepared.
Units: % w/w $$\text{Calculations } \frac{MPC \times 100}{AXC}$$

Residual excipients are defined as excipients present in the supplied protein stock material. These will typically not affect or be present at too low a concentration to affect the outcome of the precipitation process.
Methods and Materials used in Examples 4-15
Materials Glycine (G7126), L-arginine (A5006), L-glutamic Acid (G1251), trehalose dehydrate (T9531), sucrose (S7903), dextran (D9260), raffinose pentahydrate (R0250), L-serine (S4500), L-citrulline (C7629), D-gluco-6-phosphate sodium salt (G7879) and L-glutamine (G8540) were all supplied by Sigma Aldrich, Sigma-Aldrich Company Ltd, The Old Brickyard, New Road, Gillingham, Dorset.

DL-asparagine (11180), L-asparagine (11149), myo-inositol (57570), L-threonine (89180), D-glucosamine HCl (49130), N-methyl-D-glucamine (66930) were supplied by Fluka, Sigma-Aldrich Laborchemikalien GmbH, Seelze, Germany.

Propan-2-ol (296946) was supplied by BDH, VWR Hunter Boulevard, Magna Park, Lutterworth, Leicestershire.

2-Methyl-1-propanol was supplied by, Riedel-de Haën Sigma-Aldrich Laborchemikalien GmbH, Seelze, Germany.
Batch Coprecipitation Into a 125 ml Duran flask was placed the required volume of solvent, typically 47.5 mL. To this was added a 45 mm magnetic stirring bar, which had been rinsed with deionised water and dried. The flask, containing the solvent and the stirrer bar was placed on top of a magnetic stirrer (IKAMAG Mini MR), equipped with variable rotation speeds between 0-1500 rpm. At this stage the stirrer remained off.

Preparation of a Typical Coprecipitant/Protective Additive Solution was Carried out follows. Into a 7 mL vial was added a prescribed volume of protective buffer additive and a volume of deionised water diluent, pre-calculated to achieve the required concentration of protective buffer additive. To this was added the required weight of as supplied dry coprecipitant. The solution was mixed on a blood rotator unit (Stuart Rotator SB3), until all components were fully dissolved. Thereafter the pH was set to the target pH using 0.1 or 1.0M solutions of either HCl or NaOH.

This coprecipitant solution was then blended with the protein stock solution at predefined volumes—typically in a 3 mL Eppendorf tube—to achieve the protein/coprecipitant/protective additive solution that would thereafter be precipitated into the solvent. After addition of coprecipitant solution with protein stock solution, the mixture was inverted 5-10 times, to ensure thorough mixing of all components.

At this stage, the magnetic stirring speed was gradually increased to 1500 rpm, upon which the prescribed volume of protein/coprecipitant/protective additive mixture, typically 2.5 mL, was added to the solvent by steady drop wise addition. The protein/coprecipitant/protective additive mixture was added into the middle of the vortex. After the addition of all the protein/coprecipitant/protective additive mixture, the semi-formed suspension was mixed for a further 60 seconds, to ensure that all precipitation processes were complete.

After production of the suspension, the PCMC was collected over a Millipore Durapore 0.45 μm (Cat. No. HVLP0905) filter, on either a 47 mm or a 101 mm diameter, depending on how much material was prepared. Generally, for <100 mg PCMC, a 47 mm diameter membrane is sufficient; for >100 mg PCMC, the larger 101 mm diameter is recommended.

After harvesting by filtration, the wet PCMC cake was allowed to air dry, with no humidity control for ~16-24 hours. After drying, time=0 analysis work could commence.

Sample Filtration

All samples were filtered on Millipore Durapore PVDF (Cat. No. HVLP0905) membranes, 0.45 µm pore size. For low volumes of suspension (20-50 mL), 47 mm diameter membranes were used; for high volume of suspension (50-300 mL), 101 mm diameter membranes were used. Millipore Durapore PVDF membranes are low protein binding, which is important for the harvest of PCMC from mother suspensions.

Sample Storage & Stability Testing

After preparation samples were placed in 7 mL Trident glass vials with standard foil backed screw caps (Scientific Laboratory Supplies, TUB1220) and placed in fixed temperature incubators (Sanyo). The transfer was carried out at ambient humidity. No further humidity control was used.

Sample Reconstitution

After preparation of PCMC particles, it is necessary to characterize the protein, to assess protein integrity after coprecipitation. The first step of the process is reconstitution back into the buffer in which the protein was originally supplied. Typically, the PCMC powder is reconstituted into buffer at a target reconstitution concentration of 1 mg/mL. Firstly, it is necessary to calculate the required weight of PCMC powder—which is dependent on the theoretical protein loading (TPL) of the PCMC—that needs to be dissolved in a pre-defined volume of buffer, to yield the target reconstitution concentration. (Care must be taken not to exceed the solubility limit of coprecipitant in buffer; however this is only important for PCMC with low theoretical protein loadings, and does not apply to any of the examples reported in this document.) The analytical crystal concentration (AXC) can also be recorded at this stage, as it is required to calculate the final measured protein loading (MPL, % w/w) of the sample PCMC—see calculations above.

After addition of the pre-defined volume of buffer to the pre-defined volume of PCMC powder, the solution is mixed by gentle tumbling on a blood rotator (Stuart Rotator SB3). Typically the optical clarity of the reconstituted solution is assessed after 2 and 5 minutes at 25 revolutions per minute. The solution is ranked on a scale of 0-5, where 0 is equivalent to pure buffer solution, and 5 is a highly opaque solution, that contains a high proportion of insoluble protein aggregates.

UV Spectroscopy

Ultraviolet spectroscopy was used to determined protein concentration by measuring the UV absorption of the reconstituted sample solutions at 280 nm. Using a variable length, double bean Biomate 5 spectrophotometer (ThermoScientific), the absorbance of each solution was measured with reference to a blank buffer solution. Prior to sample measurements, calibration curves of all proteins described in this document has been constructed, simply by measuring the absorbance of known protein stock standards (diluted to 0.1 mg/ml-1.5 mg/ml) at 280 nm. Thereafter it is possible to calculate the extinction coefficient for each protein from the gradient of the UV calibration curve. Following the calculation of the calibration curve, the reconstituted samples were measured. PCMC samples were reconstituted as described above, to a target protein concentration of 1.0 mg/ml, and then were filtered through a PVDF 13 mm diameter, 0.45 µm syringe filter (Whatman, Cat. No. 6779-1304)—thus ensuring any insoluble contaminants were removed. After zeroing the UV spectrophotometer with buffer in both the sample and reference beams, samples were measured against the blank reference. Using the measured absorbance and the previously calculated extinction coefficient, the measured protein concentration (MPC) of the reconstituted sample solution was calculated.

High Performance Liquid Chromatography

High Performance Size Exclusion Chromatography (HPSEC) was used to measure the degree of aggregation of PCMC samples relative to the supplied protein stock. All blanks, standards and reconstituted PCMC samples were run on a Water Alliance 2690 HPLC system, fitted with a dual wavelength 2487 UV detector. Different size exclusion columns, mobile phases and instrument method settings were used for the proteins documented, the details of which are shown in the Table 4 below.

TABLE 4

| HP_SEC Parameters | |
|---|---|
| Protein | Alba Z730A Prosep Purified Human IgG |
| Size Exclusion Column | Tosoh TSK SW$_{XL}$ Guard Column 6.0 mm ID × 4.0 cm L (Cat 08543) Tosoh TSK G3000 SW$_{XL}$ 7.8 mm ID × 30.0 cm L (Cat 08541) |
| Mobile Phase | 0.05 M NaH$_2$PO$_4$ 0.6 M NaCl pH 7.0 (Isocratic) |
| Injection Volume (µl) | 25 |
| Flow Rate (mL/min) | 1.0 |
| Column Oven Temperature (° C.) | 25 |
| Detection Wavelength (nm) | 280 |
| Blank/Buffer | Phosphate Buffered Saline (PBS) pH 7.4 |
| Standard (mg/ml) | 1 mg/ml Alba Z730A prepared in PBS buffer |
| Run Time (min) | 20 |

PCMC samples were reconstituted as described above, to a target protein concentration of 1.0 mg/ml, and then were filtered through a PVDF 13 mm diameter, 0.45 µm syringe filter (Whatman; Cat. No. 6779-1304)—thus ensuring any insoluble contaminants were removed. Thereafter samples, along with associated blanks and standards, to ensure system suitability, were injected onto the column, following the methods detailed above. Monomer contents and MPL were calculated from the integrated chromatograms. Integration parameters were set to include all higher molecular weight species, monomer peaks and fragments, but not peaks associated with the buffer components.

Preparation of AlbaClone Coated Glycine Microcrystals

A human monoclonal antibody AlbaClone anti-D IgG cell line ESO1 FFMU purified was obtained from Alba Bioscience and was provided at a concentration of 5.0 mg/ml in phosphate buffered saline (PBS) (10 mM phosphate, 2.7 mM potassium chloride, 137 mM NaCl, pH 7.4 and 0.1% NaN$_3$). Two different samples were prepared:

1. Antibody coated glycine crystals [PTALBA_194_1]; prepared by precipitation of an aqueous mixture of the antibody and glycine on addition to excess propan-2-ol, and 2. Antibody coated glycine crystals [PTALBA_194_2]; incorporating protective additives prepared; by precipitation of an aqueous mixture of antibody, glycine, and basic protective additive, arginine, and the acidic protective additive, glutamic acid, on addition to excess propan-2-ol.

The precipitations were carried out by addition, using a Rainin EDP3 pipette, of 0.5 mL volume of the aqueous mixture to 9.5 mL of solvent in a 30 mL vial, at approximately 0.25 mL/second, whilst mixing rapidly with a 25 mm magnetic stirrer bar rotating at 1500 rpm. The concentrations of each of the components in the aqueous mixture at the point of coprecipitation are given in Table 5. Following stirring for 60 seconds the precipitated particles were collected by filtration onto a 0.45 µm Millipore Durapore PVDF membrane and allowed to air dry, with no humidity control, at approximately 22° C. (Room Temperature) for 16-24 hours.

The dry PCMC powder samples were then reconstituted back into PBS buffer at a target concentration of 1 mg/ml. The turbidity of the unfiltered reconstituted solutions was measured using a Hach Lange 2100AN turbidity meter. The protein loading of the particles was measured by determining the UV absorbance of the filtered reconstituted solution at 280 nm, using a ThermoScientific Biomate 5 UV spectrophotometer. Changes in aggregation state of the antibody within the precipitated particles were determined by comparing size exclusion chromatographs of the reconstituted material with the initial protein stock material, using a Waters Alliance 2690 Separations module using a 2487 dual wavelength detector as detailed above.

75.46%. Dehydrated antibody coated onto glycine microcrystals and associated with precipitation protective additives, arginine and glutamic acid, shows only a very small drop in monomer content from 85.94% to 84.45%. This equates to 98.3% retention of the antibody in its initial aggregation state, following precipitation with propan-2-ol, compared to 87.77 with no additive present. In both these preparations phosphate buffer and sodium chloride are also present having been included in the supplied protein solution. The data shows that the presence of these common excipients does not prevent aggregation of the antibody in the absence of the precipitation protective additives. The data also shows that the additives of the invention protect the antibody from aggregation during precipitation even when other Residual excipients are present. Thus, the use of precipitation protective additives is clearly advantageous for preparing dry powder formulations of therapeutic proteins such as human antibodies by precipitation. The additives significantly reduce the change in aggregation state that may be observed if an aggregation sensitive biomolecule is exposed to a polar solvent. The reconstituted samples were also found to be bioactive.

TABLE 5

| Formulation Composition | | | | | | | | |
|---|---|---|---|---|---|---|---|---|
| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
| PTALBA_194_1 | Z730 (2.5) | Glycine (75) | — | — | — | Phosphate, KCl, NaCl & $NaN_3$ | 3.01 | Propan-2-ol |
| PTALBA_194_2 | Z730 (2.5) | Glycine (75) | L-Arginine (10.9) | L-Glutamic Acid (9.2) | — | Phosphate, KCl, NaCl & $NaN_3$ | 2.42 | Propan-2-ol |

*Concentrations given are those in the final aqueous precipitation mixture. This mixture was mixed with solvent.

TABLE 6

| Results | | | | | |
|---|---|---|---|---|---|
| Sample Identifier | Monomer Content of Protein Stock (%) | Reconstitution Profile (Appearance 0-5) | Monomer Content @ t = 0 (%) | Monomer Conservation (%) | MPL (% w/w) |
| PTALBA_194_1 | 85.94 | 1 | 75.46 | 87.8 | 3.1 |
| PTALBA_194_2 | 85.94 | 0 | 84.45 | 98.3 | 2.5 |

These data show that for samples prepared with and without additives the measured protein loading (MPL) and the theoretical protein loading (TPL) are very similar, showing that substantially all of the solid material present within the aqueous mixture has precipitated into propan-2-ol to form particles. Thus the complete composition of the particles can be determined from the weights of each of the material present with the aqueous solution including the phosphate and salts.

The beneficial effects of the additives in reducing changes in the aggregation state of the antibody on exposure to the propan-2-ol are clear. The dehydrated antibody coated onto glycine crystals in the absence of buffer shows a decrease in the level of soluble monomeric species from 85.94% down to 75.46%.

Example 5

Effect of Varying the Amount of Additive Associated with Human Monoclonal Antibody Glycine Crystals In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), and was supplied in 20 mM histidine buffer, 0.2 mg/ml Polysorbate 80.

A sample series of antibody coated microcrystals were prepared with increasing levels of the precipitation protective additives, arginine and glutamic acid. The MPL, TPL and monomer content were measured as described in Example 4 and additionally the turbidity of the samples was measured in order to detect insoluble aggregates.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 8. Following stirring for 60 seconds the precipitated particles were collected by filtration onto a 0.45 μm Millipore Durapore PVDF membrane and allowed to air dry, with no humidity control, at approximately 22° C. (Room Temperature) for 16-24 hours.

The dry PCMC powder samples were then reconstituted back into PBS buffer at a target concentration of 1 mg/ml. The turbidity of the unfiltered reconstituted solutions was measured using a Hach Lange 2100AN turbidity meter.

TABLE 7

HP-SEC conditions

| Protein | PfmAb mAb |
|---|---|
| Size Exclusion Column | Tosoh TSK SW$_{XL}$ Guard Col 6.0 mm ID × 4.0 cm L (Cat 08543) |
| | Tosoh TSK G3000 SW$_{XL}$ 7.8 mm ID × 30.0 cm L (Cat 08541) |
| | Tosoh TSK G2000 SW$_{XL}$ 7.8 mm ID × 30 cm L (Cat 08540) |
| Mobile Phase | 0.2 M sodium phosphate buffer pH 7.0 (Isocratic) |
| Injection Volume (μl) | 20 |
| Flow Rate (mL/min) | 0.7 |
| Column Oven Temperature (° C.) | 25 |
| Detection Wavelength (nm) | 214 |
| Run Time (min) | 40 |

This method has also be applied in Examples 6-15

TABLE 8

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_64_2 | PfmAb (21.15) | Glycine (70) | L-Arginine (4.57) | L-Glutamic Acid (3.86) | — | Histidine & Polysorbate | 21.03 | Propan-2-ol |
| PFCP1_64_3 | PfmAb (21.15) | Glycine (70) | L-Arginine (9.15) | L-Glutamic Acid (7.72) | — | Histidine & Polysorbate | 19.40 | Propan-2-ol |
| PFCP1_64_4 | PfmAb (21.15) | Glycine (70) | L-Arginine (15.24) | L-Glutamic Acid (12.87) | — | Histidine & Polysorbate | 17.59 | Propan-2-ol |
| PFCP1_64_5 | PfmAb (21.15) | Glycine (70) | L-Arginine (21-3) | L-Glutamic Acid (18.02) | — | Histidine & Polysorbate | 16.08 | Propan-2-ol |
| PFCP1_64_6 | PfmAb (21.15) | Glycine (70) | L-Arginine (27.4) | L-Glutamic Acid (23.2) | — | Histidine & Polysorbate | 14.82 | Propan-2-ol |

*Concentrations given are those in the final aqueous precipitation mixture. This mixture was mixed with solvent.

Turbidity

Turbidity measurements were carried out to quantify the optical clarity of reconstituted PCMC solutions. Turbidity measurements were carried out using a 2100AN Turbidimeter (Hach-Lange, UK). The turbidimeter was calibrated with standard formazin suspensions (3, 6, 18, 30, 60, 4000 NTU) according to European Pharmacopia 5.0 method 2.2.1 (Clarity and degree of opalescence of liquids). Thereafter reconstituted sample solutions were loaded into pre-cleaning turbidity tubes that had been wiped with silicone oil to remove imperfections, and turbidity was measured, and quoted in NTU units. This method has also be applied in Examples 6-15.

The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles were determined by comparing size exclusion chromatographs of the reconstituted material to the initial protein stock material, using a Waters Alliance 2690 Separations module using a 2487 dual wavelength detector as detailed below.

TABLE 9

Results

| Sample Identifier | Monomer Content of Protein Stock (%) | Reconstitution Profile (NTU) | Monomer Content @ t = 0 (%) | Monomer Conservation (%) | MPL (% w/w) |
|---|---|---|---|---|---|
| PFCP1_64_2 | 99.65 | 14.9 | 94.34 | 94.7 | 19.76 |
| PFCP1_64_3 | 99.65 | 8.29 | 97.96 | 98.3 | 19.60 |
| PFCP1_64_4 | 99.65 | 3.93 | 99.32 | 99.7 | 18.12 |
| PFCP1_64_5 | 99.65 | 4.67 | 99.11 | 99.5 | 16.40 |
| PFCP1_64_6 | 99.65 | 4.22 | 99.33 | 99.7 | 15.27 |

The data shows that, when precipitation protective additives, arginine and glutamic acid are used at too low concentration in the aqueous precipitation mixture relative to the antibody, insufficient additive may be present during precipitation and/or incorporated into the particles to prevent significant changes in the aggregation state of the antibody. However, as the concentration is increased the monomer content gradually improves until at approximately 15 mg/ml arginine and 12 mg/ml glutamic acid, the monomer content in the particle becomes similar to the stock and remains at the same level on further increases to the additive concentration. Thus, on reaching a similar or slightly greater weight % as the aggregation sensitive molecule both in the precipitation mixture and the particles the effect is maximised. Importantly, the MPL in all the samples is close to the TPL, showing that substantially, all of the additive present in the aqueous mixture becomes incorporated into the particle. These data show that the beneficial effects of the additives in retaining the initial aggregation state of the aggregation sensitive antibody increase as their concentration at the point of precipitation increases. The proportion of additive within the precipitated particles also increases with concentration in a predictable and advantageous way.

Example 6

Comparison of the Performance of Preferred Precipitation Protective Additives During Precipitation Relative To excipients Commonly Used in Particle Formation In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

In this experimental series, the effect of precipitation protective additives during precipitation were compared to those obtained with excipients known in the art to be useful for preventing protein aggregation during drying and/or particle formation by other techniques e.g. lyophilisation, spray drying, supercritical drying etc These excipients were added at approximately the same molarity as that of the precipitation additives. However, because the excipients in the art generally have a higher molecular mass, their weight concentration during precipitation and the % w/w incorporated into the particles was generally higher than for the precipitation protective additives.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 10. Following stirring for 60 seconds the precipitated particles were collected by filtration onto a 0.45 μm Millipore Durapore PVDF membrane. The time to filter the suspensions was also measured because this is a critical parameter when considering whether precipitation can be used is a practically useful manufacturing technique. For this volume of suspension filtration, on this type of membrane, filtration times of less than 30 seconds would be considered to be practically useful. Following filtration the particles were allowed to air dry, with no humidity control, at approximately 22° C. (Room Temperature) for 16-24 hours.

The dry PCMC powder samples were then reconstituted back into PBS buffer at a target concentration of 1 mg/ml. The turbidity of the unfiltered reconstituted solutions was measured using a Hach Lange 2100AN turbidity meter, as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

TABLE 10

| | Formulation Composition | | | | | | | |
|---|---|---|---|---|---|---|---|---|
| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
| PFCP1_82_6 | PfmAb (36) | Glycine (50) | — | — | — | Histidine & Polysorbate | 41.07 | Propan-2-ol |
| PFCP1_82_1 | PfmAb (36) | Glycine (50) | — | — | Trehalose Dihydrate (25) | Histidine & Polysorbate | 31.95 | Propan-2-ol |
| PFCP1_82_3 | PfmAb (36) | Glycine (50) | — | — | Sucrose (22.6) | Histidine & Polysorbate | 32.64 | Propan-2-ol |
| PFCP1_82_4 | PfmAb (36) | Glycine (50) | — | — | Dextran (25) | Histidine & Polysorbate | 31.96 | Propan-2-ol |
| PFCP1_82_9 | PfmAb (36) | Glycine (50) | L-Arginine (5.66) | — | — | Histidine & Polysorbate | 38.58 | Propan-2-ol |
| PFCP1_82_2 | PfmAb (36) | Glycine (50) | — | — | Raffinose Pentahydrate (39.45) | Histidine & Polysorbate | 28.32 | Propan-2-ol |
| PFCP1_82_7 | PfmAb (36) | Glycine (50) | L-Arginine (5.66) | L-Glutamic Acid (4.78) | — | Histidine & Polysorbate | 36.70 | Propan-2-ol |

TABLE 10-continued

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_82_10 | PfmAb (36) | Glycine (50) | L-Arginine (5.66) | — | Trehalose Dihydrate (25.0) | Histidine & Polysorbate | 30.42 | Propan-2-ol |
| PFCP1_82_8 | PfmAb (36) | Glycine (50) | L-Arginine (5.66) | L-Glutamic Acid (4.78) | Trehalose Dihydrate (25.0) | Histidine & Polysorbate | 29.24 | Propan-2-ol |

*Concentrations given are those in the final aqueous precipitation mixture. This mixture was mixed with solvent.

TABLE 11

Results

| Sample Identifier | Time to Filter 20 ml of suspension (s) | Monomer Content of Protein Stock (%) | Reconstitution Profile (NTU) | Dissolution Time (min) | Monomer Content @ t = 0 (%) | Monomer Conservation (%) | MPL (% w/w) |
|---|---|---|---|---|---|---|---|
| PFCP1_82_6 | 1020 | 99.3 | 29.6 | >5 min @ 40 rpm on blood rotator | 82.70 | 83.3 | 16.5 |
| PFCP1_82_1 | 900 | 99.3 | 5.02 | No agitation required. Dissolves in <30 seconds | 90.87 | 91.5 | 28.5 |
| PFCP1_82_3 | — | 99.3 | 7.54 | No agitation required. Dissolves in <30 seconds | 87.99 | 88.6 | 24.5 |
| PFCP1_82_4 | 300 | 99.3 | 10.9 | >5 min @ 40 rpm on blood rotator | 92.74 | 93.4 | 25.5 |
| PFCP1_82_9 | 15 | 99.3 | 9.60 | >5 min @ 40 rpm on blood rotator | 89.53 | 90.2 | 36.2 |
| PFCP1_82_2 | 960 | 99.3 | 3.16 | No agitation required. Dissolves in <30 seconds | 98.40 | 99.1 | 30.7 |
| PFCP1_82_7 | 10 | 99.3 | 2.52 | No agitation required. Dissolves in <30 seconds | 95.65 | 96.3 | 36.0 |
| PFCP1_82_10 | 10 | 99.67 | 2.43 | No agitation required. Dissolves in <30 seconds | 99.24 | 99.6 | 35.36 |
| PFCP1_82_8 | 10 | 99.3 | 2.05 | No agitation required. Dissolves in <30 seconds | 99.24 | 99.9 | 40.8 |

These data shows that excipients typically reported to stabilise proteins during drying showed a significantly inferior performance during precipitation to that obtained with acidic and basic precipitation protective additives. For example, the preparations containing the commonly used excipients, trehalose, sucrose and dextran each showed a greater than 6.5% increase in the level of antibody aggregate. Increases of this magnitude would not be acceptable in a pharmaceutical product where the monomer content would typically be expected to be over 95%. Clearly it is therefore not possible to use the art relating to other drying techniques to predict how to best stabilise aggregation sensitive molecules during precipitation with a polar organic solvent. In comparison it can be seen that even if present at a significantly lower, sub-optimal weight concentration (see Example 5) the disclosed arginine-glutamic acid protective additive pair (PFCP1__82__7) is able to retain a monomer content of 95.65%.

At the weight concentration used, which corresponds to (31% w.w), raffinose pentahydrate was uniquely found to provide similar protection against aggregation to the disclosed acid/basic protective additive pair. However, significantly it also resulted in a particle suspension that was extremely difficult to filter, taking >30 times longer than what would typically be considered practically useful. From a commercial manufacturing process perspective such a slow filtering preparation would be considered unsuitable for particle preparation. Hence, raffinose would not be preferred as an additive for precipitating particles with a polar solvent unless it was also combined with the disclosed acidic or basic precipitation protective additives. Thus, it can be seen that only formulations that contained at least one acidic or basic protective additive could be filtered in a reasonable time (30 seconds or less). Acidic and basic precipitation protective additives, such as arginine and glutamic acid, therefore surprisingly provide an additional manufacturing advantage when preparing particles by precipitation—their inclusion makes it easier to process the particles.

Sample PFCP1_82_9, which contained only the basic protective additive, arginine, was found to produce inferior results compared to the sample PFCP1_82_7, which contained both a basic and an acidic protective additive. Therefore the data demonstrates that when preparing biomolecule coated microcrystals the use of a pair of acidic and basic precipitation protective additives with the coprecipitant (e.g. glycine) can provide improved retention of the biomolecule in its native aggregation state compared to use of a single additive and coprecipitant. It should also be noted that the protective additives were present at sub-optimal concentration (see example 5) and at significantly lower % w/w in the solution and particles than any of the common excipients tested.

Surprisingly the data for sample PFCP1_82_8 shows that provided the disclosed acidic and basic protective additives are present (even at sub-optimal levels) then addition of a further neutral excipient such as trehalose can provide a further beneficial effect—thus, in this sample retention of the monomer content was increased to 99.9% compared with 96.3% when trehalose was absent (PFCP1__82__7). This is a surprising result because when trehalose was used on its own and at the same concentration (PFCP1__82__1) the retained monomer content was much lower, 91.5%.

Example 7

Storage of PCMC in Solvent with and without Additive

In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 12. Following stirring for 60 seconds, aliquots of the resultant suspension were removed at regular intervals over an extended period of 48 hours. The precipitated particles in each aliquot were collected by filtration onto a 0.45 μm Millipore Durapore PVDF membrane and allowed to air dry, with no humidity control, at approximately 22° C. (Room Temperature) for 16-24 hours.

The dry PCMC powder samples were then reconstituted back into PBS buffer at a target concentration of 1 mg/ml. The turbidity of the unfiltered reconstituted solutions was measured using a Hach Lange 2100AN turbidity meter, as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

TABLE 12

| Formulation Composition | | | | | | | | |
|---|---|---|---|---|---|---|---|---|
| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
| PFCP1_85_1 | PfmAb (36) | Glycine (50) | — | — | — | Histidine & Polysorbate | 41.07 | Propan-2-ol |
| PFCP1_85_2 | PfmAb (36) | Glycine (50) | L-Arginine (5.66) | L-Glutamic Acid (4.78) | | Histidine & Polysorbate | 36.70 | Propan-2-ol |
| PFCP1_85_3 | PfmAb (36) | Glycine (50) | L-Arginine (11.3) | L-Glutamic Acid (9.56) | DL-Asparagine (10.96) | Histidine & Polysorbate | 30.13 | Propan-2-ol |

*Concentrations given are those in the final aqueous precipitation mixture. This mixture was mixed with solvent.

TABLE 13

| Results | | | | | | |
|---|---|---|---|---|---|---|
| Sample Identifier | Monomer Content of Protein Stock (%) | Time in Solvent (min) | Reconstitution Profile (0-5) or (NTU) | Monomer Content @ t = 0 (%) | Monomer Conservation (%) | MPL (% w/w) |
| PFCP1_85_1 | 99.43 | 0 | 7.41 | 92.31 | 92.8 | 4.90 |
| | (n = 6) | 30 | 7.91 | 91.49 | 92.0 | 5.035 |
| | | 60 | 6.25 | 89.42 | 89.8 | 4.856 |
| | | 1440 | 17.6 | 86.94 | 87.4 | 4.955 |
| | | 2880 | 52.9 | 89.48 | 89.99 | 3.32 |

TABLE 13-continued Results

| Sample Identifier | Monomer Content of Protein Stock (%) | Time in Solvent (min) | Reconstitution Profile (0-5) or (NTU) | Monomer Content @ t = 0 (%) | Monomer Conservation (%) | MPL (% w/w) |
|---|---|---|---|---|---|---|
| PFCP1_85_2 | 99.43 | 0 | 9.33 | 97.05 | 97.6 | 37.67 |
|  | (n = 6) | 30 | 12.6 | 96.87 | 97.4 | 35.36 |
|  |  | 60 | 11.4 | 97.11 | 97.7 | 36.18 |
|  |  | 1440 | 13.6 | 92.08 | 92.6 | 37.36 |
|  |  | 2880 | 22.7 | 91.57 | 92.1 | 28.76 |
| PFCP1_85_3 | 99.43 | 0 | 3.44 | 99.38 | 99.9 | 31.80 |
|  | (n = 6) | 30 | 5.78 | 99.39 | 99.9 | 32.7 |
|  |  | 60 | 7.13 | 99.41 | 99.9 | 31.92 |
|  |  | 1440 | 4.98 | 98.74 | 99.3 | 37.58 |
|  |  | 2880 | 7.59 | 95.01 | 95.5 | 27.99 |

These data demonstrate that formulations that contain the precipitation protective additives perform substantially better than without. Firstly it can be seen that in the absence of the additives a very significant proportion of the protein is lost during the precipitation, storage and isolation processes. This is shown by the measured protein loadings (MPL) of the particles obtained in example PFCP1_85_1 which is considerably less than the theoretical loadings (TPL). These particles therefore contain a lot less protein than expected and their composition does not reflect the concentration of dissolved solids present prior to precipitation. It can also be seen that further loss of soluble protein takes place on storage of the particles within the solvent. This is reflected in the higher turbidity values obtained for these samples. Such a large loss of valuable bioactive therapeutic protein would not be acceptable in a manufacturing process of a drug product.

By comparison the two formulations containing the precipitation protective additives advantageously have measured protein loadings close to the theoretical values and on storage in solvent the loadings remain approximately constant for up to 24 hours. These data demonstrate another manufacturing advantage that may result from the inclusion of protective additives within the precipitation mixture and in the precipitated particles—the yield of aggregation sensitive molecule converted into isolable precipitated particles can be much greater in the presence of the additives.

Secondly it can be seen that the formulations that contain precipitation protective additives retain a higher proportion of the antibody in monomeric form when stored in solvent over a prolonged period of time. Both PFCP1_85_2 and PFCP1_85_3 retain greater than 97% monomer following 60 mins storage in propan-2-ol. This compares to 89.4% for the additive-free preparation. In the case of PFCP1_85_3 which contains an acidic, basic and neutral precipitation protective additive >99% of the antibody is conserved in it initial aggregation state after 24 hours exposure to a polar organic solvent. The protection against aggregation is also reflected in the turbidity measurements which for PFCP1_85_3 give a value of less than 10 NTU even following storage for 48 hours in solvent.

Thus, an aggregation sensitive molecule can be stabilized against aggregation during particle formation and within particles exposed to polar solvent for prolonged periods using a formulation composition based solely on amino-acids.

Example 8

Supercritical Fluid Extraction of Suspensions of Protein Coated Microcrystals

In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 14. Following stirring for 60 seconds a 25 mL aliquot containing the precipitated particles were collected by filtration onto a 0.45 μm Millipore Durapore PVDF membrane and allowed to air dry, with no humidity control, at 22° C. (Room Temperature) for 16-24 hours. The remaining 25 mL of PCMC particle containing suspensions were extracted with supercritical fluid carbon dioxide, as described below.

Supercritical Fluid Extraction

All supercritical fluid extraction work was carried out using a SCF extraction rig supplied by Thar. The rig consists of a cooler unit (ThermoScientific Digital One), flowmeter (Siemens), high pressure P-series $CO_2$ (Thar) pump, Series III (Thar) co-solvent pump, heater (Thar), extraction vessels (100 mL & 500 mL-both from Thar) and automatic back pressure regulator (Thar). In a typical extraction, a pre-defined volume of PCMC suspension was placed into a container. This container was then loaded into one of the extraction vessels (depending on the volume of suspension), and the water/solvent was extracted to leave a finely divided, free-flowing powder.

All extractions were carried out a 45° C. and 100 bar. Supercritical carbon dioxide, from a dip-tube, liquid feed cylinder, (Cryoservice, EEC204-696-9, sterile $CO_2$), was pumped over the sample at 20 g/min, for approximately 30-120 minutes, depending on the volume of PCMC suspension from which the water/solvent was extracted. After the extraction process was carried out, it was necessary to depressurize which takes approximately 30 minutes. After depressurization, the extraction vessel was opened, and the container containing the extracted PCMC powder was lifted out. The container was opened and the contents were collected into a pre-weighed vial. Thereafter the sample analysis was started. The total weight of $CO_2$ used in each extraction was recorded from the $CO_2$ flow meter.

The dry PCMC powder samples were there reconstituted back into PBS buffer at a target concentration of 1 mg/ml. The appearance was determined as described in Example 4; the turbidity of the unfiltered reconstituted solutions was measured using a Hach Lange 2100AN turbidity meter as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

dioxide (PFCP1_46_0_2M1P_SCF) that the extraction process further decreases the monomer content of the antibody from 94.21% to 86.42%. Thus, exposure of particles containing an aggregation sensitive molecule to supercritical fluid carbon dioxide can lead to a detrimental decrease in the proportion of the molecule in the original aggregation state. Since it has been shown that supercritical fluid extraction is an attractive method for converting suspensions of particles in solvent to dry powders with improved aerodynamic properties it would be beneficial to be able to prevent or alleviate this loss.

It can be seen from the data collected for PFCP1_46_2_FIL and PFCP1_46_2_SCF that the presence of the precipitation protective additives leads to a dramatic improvement in monomer conservation following filtration, as described in previous examples, but also following supercritical fluid extraction. Thus, in sample PFCP1_46_0_

TABLE 14

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_46_0_2M1P_FIL | PfmAb (36) | Glycine (50) | — | — | — | Histidine & Polysorbate | 41.07 | 2-Methyl-1-Propanol |
| PFCP1_46_0_2M1P_SCF | PfmAb (36) | Glycine (50) | — | — | — | Histidine & Polysorbate | 41.07 | 2-Methyl-1-Propanol |
| PFCP1_46_2_FIL | PfmAb (36) | Glycine (50) | L-Arginine (11.3) | L-Glutamic Acid (9.6) | — | Histidine & Polysorbate | 32.7 | 2-Methyl-1-Propanol |
| PFCP1_46_2_SCF | PfmAb (36) | Glycine (50) | L-Arginine (11.3) | L-Glutamic Acid (9.6) | — | Histidine & Polysorbate | 32.7 | 2-Methyl-1-Propanol |

*Concentrations given are those in the final aqueous precipitation mixture. This mixture was mixed with solvent.

TABLE 15

Results

| Sample Identifier | Monomer Content of Protein Stock (%) | Reconstitution Profile (NTU) or (Appearnce 0-5) | Monomer Content @ t = 0 (%) | Monomer Conservation (%) | MPL (% w/w) |
|---|---|---|---|---|---|
| PFCP1_46_0_2M1P_FIL | 99.56 | 5.15 | 94.21 | 94.6 | 39.7 |
| PFCP1_46_0_2M1P_SCF | 99.56 | 32.00 | 86.42 | 86.8 | 25.0 |
| PFCP1_46_2_FIL | 99.59 | Appearance 0 | 99.55 | 99.95 | 31.86 |
| PFCP1_46_2_SCF | 99.59 | Appearance 0 | 99.43 | 99.8 | 33.02 |

The data demonstrates that the presence of the precipitation protective additives, arginine:glutamic acid, within particles leads to much better retention of antibody monomer content on extraction of a suspension of antibody coated microcrystals, with supercritical fluid carbon dioxide It can be seen by comparison of the data for the filtered sample prepared without additive (PFCP1_46_2M1P_FIL) and the same sample extracted with super-critical fluid carbon dioxide (PFCP1_46_0_2M1P_SCF) that the extraction process further decreases the monomer content of the antibody from 94.21% to 86.42%.

2M1P_SCF, that contains no additive, 86.8% monomer is retained after supercritical drying, whilst in sample PFCP1_46_2_SCF that contains arginine and glutamic acid, 99.8% of monomer is retained after supercritical drying.

Clearly, the presence of protective additives is pivotal and offers significant advantages when extracting suspensions of particles that contain aggregation sensitive molecules with supercritical fluids

Example 9

Combinations of Acid, Basic and Neutral Precipitation Protective Additives Types In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 16. Following stirring for 60 seconds a 25 mL aliquot containing the precipitated particles were collected by filtration onto a 0.45 μm Millipore Durapore PVDF membrane and allowed to air dry, with no humidity control, at 22° C. (Room Temperature) for 16-24 hours.

The dry PCMC powder samples were then reconstituted back into PBS buffer at a target concentration of 1 mg/ml. The turbidity of the unfiltered reconstituted solutions was measured using a Hach Lange 2100AN turbidity meter, as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

TABLE 16

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_76_9 | PfmAb (36) | Glycine (50) | — | — | — | Histidine & Polysorbate | 41.07 | Propan-2-ol |
| PFCP1_68_1 | PfmAb (36) | Glycine (50) | L-Arginine (5.66) | L-Glutamic Acid (4.78) | — | Histidine & Polysorbate | 36.21 | Propan-2-ol |
| PFCP1_68_5 | PfmAb (36) | Glycine (50) | L-Arginine (5.66) | L-Glutamic Acid (4.78) | DL-Asparagine (10.97) | Histidine & Polysorbate | 32.55 | Propan-2-ol |
| PFCP1_68_7 | PfmAb (36) | Glycine (50) | L-Arginine (5.66) | L-Glutamic Acid (4.78) | Trehalose Dihydrate (25) | Histidine & Polysorbate | 28.81 | Propan-2-ol |
| PFCP1_68_8 | PfmAb (36) | Glycine (50) | L-Arginine (5.66) | L-Glutamic Acid (4.78) | L-Serine (7.68) | Histidine & Polysorbate | 33.57 | Propan-2-ol |
| PFCP1_68_11 | PfmAb (36) | Glycine (50) | L-Arginine (5.66) | L-Glutamic Acid (4.78) | L-Asparagine (9.65) | Histidine & Polysorbate | 32.95 | Propan-2-ol |
| PFCP1_68_13 | PfmAb (36) | Glycine (50) | L-Arginine (5.66) | L-Glutamic Acid (4.78) | Myo-inositol (13.16) | Histidine & Polysorbate | 31.90 | Propan-2-ol |
| PFCP1_68_14 | PfmAb (36) | Glycine (50) | L-Arginine (5.66) | L-Glutamic Acid (4.78) | Raffinose Pentahydrate (43.4) | Histidine & Polysorbate | 25.05 | Propan-2-ol |
| PFCP1_68_16 | PfmAb (36) | Glycine (50) | L-Arginine (5.66) | L-Glutamic Acid (4.78) | L-Citrulline (12.8) | Histidine & Polysorbate | 32.0 | Propan-2-ol |
| PFCP1_68_20 | PfmAb (36) | Glycine (50) | L-Arginine (5.66) | L-Glutamic Acid (4.78) | Dextran (25) | Histidine & Polysorbate | 28.81 | Propan-2-ol |
| PFCP1_68_15 | PfmAb (36) | Glycine (50) | L-Arginine (5.66) | L-Glutamic Acid (4.78) | L-Threonine (8.7) | Histidine & Polysorbate | 33.24 | Propan-2-ol |
| PFCP1_68_2 | PfmAb (36) | Glycine (50) | L-Arginine (5.66) | L-Glutamic Acid (4.78) | Sodium sulfate (10.4) | Histidine & Polysorbate | 32.724 | Propan-2-ol |

TABLE 16-continued

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_76_1 | PfmAb (36) | Glycine (50) | D-Glucos-amine HCl (7.04) | D-gluco-6-phosphate sodium salt (9.17) | — | Histidine & Polysorbate | 34.66 | Propan-2-ol |
| PFCP1_76_2 | PfmAb (36) | Glycine (50) | | D-gluco-6-phosphate sodium salt (9.17) | L-Citrulline (5.69) | Histidine & Polysorbate | 35.12 | Propan-2-ol |
| PFCP1_76_5 | PfmAb (36) | Glycine (50) | N-Methyl-D-Glucamine (3.74) | D-gluco-6-phosphate sodium salt (9.17) | — | Histidine & Polysorbate | 35.80 | Propan-2-ol |
| PFCP1_76_6 | PfmAb (36) | Glycine (50) | L-Arginine (11.33) | L-Glutamic Acid (9.56) | L-Citrulline (12.80) | Histidine & Polysorbate | 29.67 | Propan-2-ol |

Concentrations given are those in the final aqueous precipitation mixture. This mixture was mixed with solvent.

TABLE 17

Results

| Sample Identifier | Monomer Content of Protein Stock (%) | Reconstitution Profile (0-5) or (NTU) | Monomer Content @ t = 0 (%) | Monomer Conservation (%) | MPL (% w/w) |
|---|---|---|---|---|---|
| PFCP1_76_9 | 99.5 | 4.91 | 86.26 | 86.69 | 29.53 |
| PFCP1_68_1 | 99.54 | 2.75 | 96.50 | 96.98 | 35.81 |
| PFCP1_68_5 | 99.54 | 2.11 | 98.72 | 99.18 | 32.55 |
| PFCP1_68_7 | 99.54 | 3.11 | 99.43 | 99.89 | 32.18 |
| PFCP1_68_8 | 99.54 | 2.00 | 97.17 | 97.62 | 36.60 |
| PFCP1_68_11 | 99.54 | 3.02 | 95.67 | 96.11 | 33.31 |
| PFCP1_68_13 | 99.54 | 2.95 | 99.12 | 99.58 | 34.00 |
| PFCP1_68_14 | 99.54 | 3.02 | 99.45 | 99.90 | 29.21 |
| PFCP1_68_16 | 99.54 | 1.90 | 98.13 | 98.58 | 33.90 |
| PFCP1_68_20 | 99.54 | 2.54 | 97.93 | 98.38 | 28.28 |
| PFCP1_68_15 | 99.54 | 2.88 | 93.70 | 94.13 | 33.61 |
| PFCP1_68_2 | 99.54 | 3.47 | 94.64 | 95.08 | 32.08 |
| PFCP1_76_1 | 99.5 | 2.00 | 97.47 | 97.96 | 35.25 |
| PFCP1_76_2 | 99.5 | 2.14 | 96.36 | 96.94 | 35.81 |
| PFCP1_76_5 | 99.5 | 2.08 | 97.14 | 97.63 | 36.48 |
| PFCP1_76_6 | 99.5 | 1.77 | 98.65 | 99.15 | 32.24 |

These data demonstrate that different combinations of precipitation protective additives can be used to stabilize an aggregation sensitive molecule during the formation of and within precipitated particles exposed to polar solvents. Thus, there are provided examples of particles containing an acidic additive with a basic additive, an acidic additive with a neutral additive and numerous examples of particles containing acidic, basic and neutral additives. Formulations that contain both an acidic and basic protective additive typically provide improved stabilisation over those where only one of the components is present. It should be noted that the weight percentage of the acidic and basic protective additives within these formulations has been deliberately kept below their optimal values so that any additional benefits provided by the neutral additives could be observed. The surprisingly much poorer stabilisation provided by commonly used neutral additives, such as trehalose and dextran, when used on their own, was demonstrated in Example 6. It can be seen that when combined with an acidic and basic protective additive the neutral additives DL-asparagine, trehalose, serine myoinositol, raffinose pentahydrate, citrulline and dextran are advantageous and provide particularly beneficial effects. Conversely, sodium sulfate has no beneficial effects.

The data also demonstrates that other combinations of acidic and basic additives can be advantageously used to stabilise aggregation sensitive molecules such as N-Methyl-D-Glucamine with D-gluco-6-phosphate. Amino-acid based protective additives such as the arginine:glutamic acid additive pair may be preferred for applications requiring long term storage of biomolecules at room-temperature or above because they will be less prone to cyclise or react with surface residues on the protein than for example sugar acids or sugar bases.

Example 10

High Loaded (No Coprecipitant) Particles

In this example the aggregation sensitive bioactive molecule used was a human monoclonal antibody, PfmAb, obtained from Pfizer Inc, Chesterfield, St Louis, Mo. This antibody is an IgG$_2$ isotype and binds to human cytotoxic T lymphocyte-associated antigen 4 (CTLA-4, CD152), supplied in 20 mM histidine buffer, 0.2 mg/ml Polysorbate 80.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 min magnetic stirrer bar rotating at 1500 rpm. The concentrations of each of the components at the point of coprecipitation are given in Table 18. Following stirring for 60 seconds a 25 mL aliquot containing the precipitated particles were collected by filtration onto a 0.45 μm Millipore Durapore PVDF membrane and allowed to air dry, with no humidity control, at 22° C. (Room Temperature) for 16-24 hours.

Portions of the samples were analyzed immediately following drying (t=0) or else following storage for 13 weeks in screw-capped vials kept at 40° C. (t=13 weeks).

The dry PCMC powder samples were there reconstituted back into PBS buffer at a target concentration of 1 mg/ml. The appearance was determined as described in Example 4; the turbidity of the unfiltered reconstituted solutions was measured using a Hach Lange 2100AN turbidity meter as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

When these samples were subjected to accelerated stress conditions it was clear that the formulation which contained protective additives, was significantly more resistance to aggregation of the bioactive antibody, and after 13 weeks at 40° C., was still 92.65% monomer. The sample without protective additive was only 81.5% monomer after the same incubation period at 40° C.

It should be noted that samples precipitated without coprecipitant are generally less stable on storage at high tempera-

TABLE 18

| | Formulation Composition | | | | | | | |
|---|---|---|---|---|---|---|---|---|
| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
| PFCP1_41_2 | PfmAb (45.3) | — | — | — | — | Histidine & Polysorbate | 95.52 | 2-Methyl-1-Propanol |
| PFCP1_41_1 | PfmAb (45.3) | — | L-Arginine (6.22) | L-Glutamic Acid (5.25) | — | Histidine & Polysorbate | 76.92 | 2-Methyl-1-Propanol |

*Concentrations given are those in the final aqueous precipitation mixture. This mixture was mixed with solvent.

TABLE 19

| | Results | | | | |
|---|---|---|---|---|---|
| Sample Identifier | Monomer Content of Protein Stock (%) | Reconstitution Profile (Appearance 0-5) | Monomer Content @ t = 0 (%) | Monomer Conservation (%) | MPL (% w/w) |
| PFCP1_41_2 | 99.515 | Appearance 0 | 91.49 | 91.9 | 82.8 |
| PFCP1_41_1 | 99.515 | Appearance 0 | 98.8 | 99.3 | 71.3 |

TABLE 20

| | Results from Accelerated Stability Study | | | | | |
|---|---|---|---|---|---|---|
| Sample Identifier | Monomer Content of Protein Stock (%) | Reconstitution Profile (NTU) | Monomer Content @ t = 13 weeks (%) | Monomer Conservation @ t = 13 weeks (%) | MPL (% w/w) | % Change in Monomer Content over Time Period (%) |
| PFCP1_41_2 | 99.515 | 6.94 | 81.15 | 81.5 | 83.59 | −11.3 |
| PFCP1_41_1 | 99.515 | 1.90 | 92.65 | 93.1 (13 weeks) | 73.08 | −6.3 |

The data shows that using a pair of acidic and basic protective additives it is possible to coprecipitate antibody by addition into solvent to form antibody particles in which a high amount of monomer has been retained at t=0: In these samples there is no coprecipitant present, hence, a crystalline core will not form and the protein content of the particles is consequently much higher. Typically particles with protein contents greater than 50% w/w can be prepared. In this example the antibody particles containing the additives have a protein loading of >70% w/w. Precipitating just antibody, without protective additives or coprecipitant, leads to a material which contains significantly less monomer at t=0.

ture than those precipitated with one present—see stability data for PFCP1_8_4 with coprecipitant glycine and PFCP1_8_8 with coprecipitant glutamine in Example 11. In the presence of a coprecipitant and with the same acidic and basic protective additive monomer contents of greater than 96% can be retained even after 26 weeks at 40° C.

These particles have high protein loadings and therefore may be advantageous in formulations that require delivery of very high concentrations of protein to an animal or human.

Example 11

Stability Data

In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 21. Following stirring for 60 seconds a 25 mL aliquot containing the precipitated particles were collected by filtration onto a 0.45 μm Millipore Durapore PVDF membrane and allowed to air dry, with no humidity control, at 22° C. (Room Temperature) for 16-24 hours.

Portions of the samples were analyzed immediately following drying (t=0) or else following storage for periods of 7, 13 and 26 weeks in foil-backed screw-capped vials kept at 40° C.

The dry PCMC powder samples were there reconstituted back into PBS buffer at a target concentration of 1 mg/ml. The appearance was determined as described in Example 4; the turbidity of the unfiltered reconstituted solutions was measured using a Hach Lange 2100AN turbidity meter as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

TABLE 22

| | Results | | | | |
|---|---|---|---|---|---|
| Sample Identifier | Monomer Content of Protein Stock (%) | Reconstitution Profile (Appearance 0-5) | Monomer Content as % at t = 0 | Monomer Conservation (%) | MPL (% w/w) |
| PFCP1_39_1 | 99.495 | Appearance 0 | 94.92 | 95.4 | 16.5 |
| PFCP1_39_2 | 99.495 | Appearance 0 | 94.04 | 98.5 | 17.1 |
| PFCP1_39_3 | 99.495 | Appearance 0 | 98.81 | 99.3 | 17.4 |
| PFCP1_39_4 | 99.495 | Appearance 0 | 99.18 | 99.7 | 16.03 |
| PFCP1_5_2 | 99.51 | Appearance 0 | 81.99 | 82.4 | 8.37 |
| PFCP1_5_1 | 99.51 | Appearance 0 | 93.65 | 94.1 | 16.08 |
| PFCP1_8_3 | 99.57 | Appearance 0 | 97.87 | 98.3 | 34.38 |
| PFCP1_8_4 | 99.57 | Appearance 0 | 98.95 | 99.4 | 35.31 |
| PFCP1_8_7 | 99.57 | Appearance 0 | 99.36 | 99.8 | 36.23 |
| PFCP1_8_8 | 99.57 | Appearance 0 | 99.59 | 100 | 31.29 |
| PFCP1_8_9 | 99.57 | Appearance 1 | 78.77 | 79.1 | 32.25 |
| PFCP1_8_10 | 99.57 | Appearance 0 | 99.61 | 100 | 34.21 |

TABLE 21

| | Formulation Composition | | | | | | | |
|---|---|---|---|---|---|---|---|---|
| Sample Identifier | (a) (mg/ml) | (b) (mg/ml) | (c) (mg/ml) | (d) (mg/ml) | (e) (mg/ml) | TPL (% w/w) | Solvent | Storage Temp. |
| PFCP1_39_1 | 21.15 | 70 | 3.04 | 2.57 | 14 | 18.92 | Propan-2-ol | 25 |
| PFCP1_39_2 | 21.15 | 70 | 3.04 | 2.57 | 28 | 16.82 | Propan-2-ol | 25 |
| PFCP1_39_3 | 21.15 | 70 | 9.14 | 7.72 | 14 | 17.19 | Propan-2-ol | 25 |
| PFCP1_39_4 | 21.15 | 70 | 9.14 | 7.72 | 28 | 15.44 | Propan-2-ol | 25 |
| PFCP1-39_5_2 | 22.58 | 101.9 | — | — | — | 17.99 | Propan-2-ol | 40 |
| PFCP1-39_5_1 | 22.58 | 101.9 | — | — | — | 17.99 | 2-Methyl-1-Propanol | 40 |

(a) - Bioactive Molecule (pfmAb)
(b) - Co-precipitant (Glycine)
(c) - Basic Addidtive (L-Arginine)
(d) - Acidic Additive (L-Glutamic Acid)
(e) - Neutral Additive (Trehalose Dihydrate)

Residual trace excipients (Histidine and Polysorbate) were present in each sample.

TABLE 23

| | Results from Accelerated Stability Study | | | | | |
|---|---|---|---|---|---|---|
| Sample Identifier | Monomer Content of Protein Stock (%) | Reconstitution Profile (Appearance 0-5) or (NTU) | Monomer Content as % (weeks in storage) | % Monomer content conserved (weeks in storage) | MPL (% w/w) | % Change in Monomer Content over Time Period (%) |
| PFCP1_39_1 | 99.495 | Appearance 0 | 95.32 (7 weeks) | 95.8 (7 weeks) | 17.27 | +0.9 |
| PFCP1_39_2 | 99.495 | Appearance 0 | 97.88 (7 weeks) | 99.0 (7 weeks) | 18.82 | −0.2 |

TABLE 23-continued

Results from Accelerated Stability Study

| Sample Identifier | Monomer Content of Protein Stock (%) | Reconstitution Profile (Appearance 0-5) or (NTU) | Monomer Content as % (weeks in storage) | % Monomer content conserved (weeks in storage) | MPL (% w/w) | % Change in Monomer Content over Time Period (%) |
|---|---|---|---|---|---|---|
| PFCP1_39_3 | 99.495 | Appearance 0 | 98.74 (7 weeks) | 99.2 (7 weeks) | 19.43 | −0.07 |
| PFCP1_39_4 | 99.495 | Appearance 0 | 99.13 (7 weeks) | 99.6 (7 weeks) | 18.98 | −0.05 |
| PFCP1_5_2 | 99.57 | Appearance 4 | 74.54 (13 weeks) | 74.9 (13 weeks) | 8.08 | −9.1 |
| PFCP1_5_1 | 99.57 | Appearance 0 | 84.83 (13 weeks) | 85.2 (13 weeks) | 17.55 | −9.4 |
| PFCP1_8_3 | 99.57 | 2.3 | 92.79 (26 weeks) | 93.2 (26 weeks) | 33.25 | −5.2 |
| PFCP1_8_4 | 99.57 | 2.51 | 96.3 (26 weeks) | 96.7 (26 weeks) | 37.75 | −2.7 |
| PFCP1_8_7 | 99.57 | 6.8 | 96.33 (26 weeks) | 96.7 (26 weeks) | 34.7 | −3.0 |
| PFCP1_8_8 | 99.57 | 3.62 | 97.76 (26 weeks) | 98.2 (26 weeks) | 32.23 | −1.8 |
| PFCP1_8_9 | 99.57 | 27.5 | 78.44 (26 weeks) | 78.8 (26 weeks) | 29.1 | −0.4 |
| PFCP1_8_10 | 99.57 | 2.5 | 94.06 (26 weeks) | 94.5 (26 weeks) | 33.23 | −5.6 |

These data demonstrate how the association of the acidic and basic precipitation protective additives with particles increases the stability of an aggregation sensitive antibody following storage at elevated temperatures. Comparison of those samples containing acidic and basic additives with samples precipitated with either no additive or with the neutral additive trehalose shows the clear benefits of the acid/basic additives pair in protecting the antibody against aggregation. Thus, PFCP1__5__1 which contains no additive has lost 14.8% of the original monomer content after 13 weeks at 40° C. while PFCP1__8__4 containing arginine and glutamic acid has only lost 3.3% after 26 weeks at 40° C. Sample PFCP1__8__3 which consists of antibody coated glycine particles containing arginine and glutamic acid, precipitated from propanol, retains 93.2% of the original monomer after 26 weeks at 40° C. while sample PFCP1__8__9 which consists of antibody coated glycine particles containing trehalose, precipitated from propanol, retains only 78.8% monomer after 26 weeks. Bioactivity data measured by ELISA typically showed high retention of activity for samples exhibiting high monomer contents. These data therefore demonstrate the utility of protective buffer pairs for extending the shelf-life of antibody based products including biopharmaceutical and diagnostic products.

These data also demonstrate that the advantageous effects are more pronounced when precipitating particles from the more polar solvent, propan-2-ol than with 2-methyl-1-propanol. This is because the latter solvent appears to have a less detrimental effect on protein integrity and aggregation state even when additives are not present. 2-methyl-1-propanol may therefore be a preferred solvent for use with the additives when working with highly aggregation sensitive molecules It has also been discovered that for preparing small dry particles that have median particles sizes in the range 2-15 μm (measured with Sympatec HELOS Particle sizer), it is generally more advantageous to use propan-2-ol than 2-methyl-1-propanol (see Example 13). Clearly therefore, in order to ensure high protein integrity after prolonged storage within fine dry powders, it is particularly advantageous to incorporate precipitation protective additives. Fine dry powders of therapeutic biomolecules can be used for non-invasive delivery by for example nasal or pulmonary delivery.

Storing samples @−20° C.

TABLE 24

| Formulation Composition | | | | | | | | |
|---|---|---|---|---|---|---|---|---|
| Sample Identifier | (a) (mg/ml) | (b) (mg/ml) | (c) (mg/ml) | (d) (mg/ml) | (e) (mg/ml) | TPL (% w/w) | Solvent | Storage Temperature |
| PFCP1_100_1 | (36) | (50) | — | — | — | 41.07 | Propan-2-ol | 25 |
| PFCP1_100_2 | (36) | (70) | 11.3) | (9.6) | — | 33.17 | Propan-2-ol | 25 |

(a) - Bioactive Molecule (pfmAb)
(b) - Co-precipitant (Glycine)
(c) - Basic Additive (L-Arginine)
(d) - Acidic Additive (L-Glutamic Acid)
(e) - Neutral Additive (Trehalose Dihydrate)

Residual trace excipients (Histidine and Polysorbate) were present in each sample.

Concentrations given are those in the final aqueous precipitation mixture. This mixture was mixed with solvent.

TABLE 25

Results

| Sample Identifier | Monomer Content of Protein Stock (%) | Reconstitution Profile (Appearance 0-5) or (NTU) | Monomer Content as % After 48 hrs @ −20° C.) | % Monomer content conserved (weeks in storage) | MPL (% w/w) |
|---|---|---|---|---|---|
| PFCP1_100_1 | 99.72 | 17.3 | 82.16 | 82.4 | 21.38 |
| PFCP1_100_2 | 99.72 | 2.18 | 99.54 | 99.8 | 33.54 |

The data shows PCMC can also be stored at −20° C. with no detrimental effects, so long as protective additive is included in the formulation.

Example 12

Formation of Particles by Continuous Process

In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The batch precipitations were carried out by addition, using a Rainin EDP3 pipette, of 2.5 mL volume of the aqueous mixture to 47.5 mL of solvent in a 125 mL vial, at 0.25 mL/second, whilst mixing rapidly with a 45 mm magnetic stirrer bar rotating at 1500 rpm. Following stirring for 60 seconds a 25 mL aliquot containing the precipitated particles were collected by filtration onto a 0.45 μm Millipore Durapore PVDF membrane and allowed to air dry, with no humidity control, at 22° C. (Room Temperature) for 16-24 hours. The continuous flow precipitation were prepared on a bespoke continuous flow coprecipitation process, operating at a total flow rate of 3000 mL/min.

Continuous Precipitation

Several samples were prepared using a Continuous Flow Coprecipitation system, which provides a preferred method for scaling up the batch coprecipitation process. Preparation of protein/coprecipitant/protective additive mixture is identical, except that for continuous flow coprecipitation, the volumes involved are usually significantly higher.

The continuous flow coprecipitation system consists of two pump drive units (Watson Marlow 520DU), one fitted with a low pressure 505L (Watson Marlow) offset track pumphead (for the protein/coprecipitant/protective additive mixture); the other with a high pressure (0-4 bar) 520 REH (Watson Marlow) pumphead (for the solvent). Both are equipped with elements (Marprene) of 3.2 mm and 6.4 mm respectively. A 3.1 mm ID cross-piece mixer (Kartell) was then connected as follows. The protein/coprecipitant/protective additive mixture was delivered by the first branch inlet, via 3.2 mm (platinum cured) silicone tubing. The solvent, which was pre-split into two equal flows by a 6.4 mm Y-branch (Kartell), was then introduced into the cross piece mixer perpendicularly, such that the solvent flows are opposed (branches 2 & 3)—to form a double jet impingement mixing environment. The fourth branch of the cross-piece mixer forms the outlet, where the PCMC suspension exits into a 3.2 mm end tube, of approximately 1 m in length. A 100 mL burette and solvent aspirator served as reservoirs for the protein/coprecipitant/protective additive mixture and solvent respectively. Feed tubing from solvent aspirator to pump was a 6.4 mm silicone tube; feed tubing from protein/coprecipitant/protective additive mixture burette to pump was a 3.2 mm silicone tube. Both feed tubing incorporated a non-return valve (Kartell). Also incorporated into the solvent line is a pressure gauge (Wika) capable of measuring pressure from 0-6 bar, in 0.2 bar increments.

In a typical PCMC coprecipitation the protein/coprecipitant/protective additive mixture to solvent volumes ratio is 5.0% v/v. Therefore of the total flow rate, 5% must be protein/coprecipitant/protective additive mixture; 95% must be solvent. Prior to starting the calibration curve is used to determine the required rpm settings for the protein/coprecipitant/protective additive mixture pump and the solvent pump. In the example included in this document, the total flow rate was 3000 mL/min, thus the protein/coprecipitant/protective additive mixture flowrate was 150 mL/min; the solvent flowrate was 2850 mL/min. Thereafter each pump is primed with the relevant feed stock.

On simultaneous start-up of both pumps, the PCMC suspension instantaneously begins to form when the protein/coprecipitant/protective additive mixture makes contact with solvent. However, the first 5-50 system dwell volumes (depending on availability of quantity of protein/coprecipitant/protective additive mixture feedstock) of the newly forming suspension is discarded, such that any PCMC harvested are representative and fully formed. During production, both flow rate and pressure are routinely monitored, such that a pressure curve and flow rate graph as a function of production time can be constructed. This allows the detection of fouling or blockage issues. Typically however, all formulations described did not result in any blockage phenomena.

The concentrations of each of the components at the point of coprecipitation are given in Table 24.

Portions of the samples were analyzed immediately following drying (t=0) or else following storage for a periods of 13 weeks in foil-backed screw-capped vials kept at 40° C.

The dry PCMC powder samples were there reconstituted back into PBS buffer at a target concentration of 1 mg/ml. The appearance was determined as described in Example 4; the turbidity of the unfiltered reconstituted solutions was measured using a Hach Lange 2100AN turbidity meter as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The batch precipitations were carried out by addition, using a Rainin EDP3 pipette, of 2.5 mL volume of the aqueous mixture to 47.5 mL of solvent in a 125 mL vial, at 0.25

TABLE 26

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_17_1_ BATCH | PfmAb (21.88) | L-Glutamine (17.24) | L-Arginine (15.01) | L-Glutamic Acid (12.68) | — | Histidine & Polysorbate | 32.25 | 2-Methyl-1-Propanol |
| PFCP1_17_1_ CONTINUOUS | PfmAb (21.88) | L-Glutamine (17.24 | L-Arginine (15.01) | L-Glutamic Acid (12.68) | — | Histidine & Polysorbate | 32.25 | 2-Methyl-1-Propanol |

*Concentrations given are those in the final aqueous precipitation mixture. This mixture was mixed with solvent.

TABLE 27

Results

| Sample Identifier | Monomer Content of Protein Stock (%) | Reconstitution Profile (Appearance 0-5) | Monomer Content @ t = 0 (%) | Monomer Conservation (%) | MPL (% w/w) |
|---|---|---|---|---|---|
| PFCP1_17_1_ BATCH | 99.35 | Appearance 0 | 99.19 | 99.8 | 29.22 |
| PFCP1_17_1_ CONTINUOUS | 99.35 | Appearance 0 | 99.14 | 99.8 | 33.78 |

TABLE 28

Results from Accelerated Stability Study

| Sample Identifier | Monomer Content of Protein Stock (%) | Reconstitution Profile (NTU) | Monomer Content as % (weeks in storage) | % Monomer content conserved (weeks in storage) | MPL (% w/w) | % Change in Monomer Content over Time Period (%) |
|---|---|---|---|---|---|---|
| PFCP1_17_1_ BATCH | 99.35 | 2.41 | 99.34 (13 weeks) | 99.99 (13 weeks) | 27.72 | +0.15 |
| PFCP1_17_1_ CONTINUOUS | 99.35 | 6.00 | 98.38 (13 weeks) | 99.0 (13 weeks) | 29.02 | −0.77 |

These data shows that antibody particles containing the arginine:glutamic acid protective additive pair can be prepared using both a batch precipitation or continuous precipitation format. Equivalent material is produced by the two processes with high protein integrity (low turbidity and high monomer content) and good long term stability profiles. The continuous flow precipitation format offers particular advantages for scale-up of the antibody particle production process. These data demonstrate that the disclosed additives may be advantageously used for processing large quantities of precipitated particles suitable for clinical trials or for commercial manufacture of products including drug products.

Example 13

Sizes of Additive-Containing Particles

In this example the aggregation sensitive bioactive molecule used was a human monoclonal antibody, PfmAb, obtained from Pfizer Inc, Chesterfield, St Louis, Mo. This mL/second, whilst mixing rapidly with a 45 mm magnetic stirrer bar rotating at 1500 rpm. The concentrations of each of the components at the point of coprecipitation are given in Table 27. Following stirring for 60 seconds a 25 mL aliquot containing the precipitated particles were collected by filtration onto a 0.45 µM Millipore Durapore PVDF membrane and allowed to air dry, with no humidity control, at 22° C. (Room Temperature) for 16-24 hours.

Portions of the samples were analyzed immediately following drying (t=0) or else following storage for periods of 7, 13 and 26 weeks in foil-backed screw-capped vials kept at 40° C.

The dry PCMC powder samples were there reconstituted back into PBS buffer at a target concentration of 1 mg/ml. The appearance was determined as described in Example 4. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

Particle size was measured using a Sympatec Helos Laser bench, utilising a ASPIROS/RODOS/M sampling dispersion unit.

Particle Size Measurements

Dry powder particle size measurements were made using a Sympatec HELOS Particle Sizer, fitted with a R2 lens system (capable of particle size measurement from 0.25-87.5 µm) and equipped with an ASPIROS sampling unit and RODOS/M disperser unit. Prior to sample analysis, the lenses and dust covers were thoroughly cleaned and the system was regularly calibrated using silicon carbide standards (SiC-F1200'03; Sympatec). Operating at a dispersion pressure of 1 bar and a sample feed rate of 20-50 mm/s, approximately 30-40 milligrams of dry PCMC powder was introduced into the system. Median particle size (×50) and particle population span ((×90-×10)/×50) were recorded for all samples measurements.

2-ol it is possible to prepare particles which have a median size in the range 1-15 microns which may be suitable for delivery by inhalation. Using 2-methyl-1-propanol it is possible to prepare larger particles which have a median size in the range 5-100 microns. The larger particles may be advantageously used in applications where the particles are coated to alter the release profile of a bioactive molecule from the particles, such as a sustained release formulation. The stability data shows that the protective additives provide high stability towards aggregation of the antibody in both small and large particles.

Example 14

Combinations of Sugar Based and Amino-Acid Based Basic and Acidic Protective Additives In this example the aggregation sensitive bioactive molecule used was a human monoclonal antibody, PfmAb, obtained from Pfizer Inc, Chesterfield, St Louis, Mo. This

TABLE 29

| Formulation Composition | | | | | | | | |
|---|---|---|---|---|---|---|---|---|
| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
| PFCP1_46_1 | PfmAb (35.25) | Glycine (50) | L-Arginine (11.3) | L-Glutamic Acid (9.6) | — | Histidine & Polysorbate | 32.7 | Propan-2-ol |
| PFCP1_46_2 | PfmAb (35.25) | Glycine (50) | L-Arginine (11.3) | L-Glutamic Acid (9.6) | — | Histidine & Polysorbate | 32.7 | 2-Methyl-1-Propanol |

*Concentrations given are those in the final aqueous precipitation mixture. This mixture was mixed with solvent.

TABLE 30

| Results | | | | | | |
|---|---|---|---|---|---|---|
| Sample Identifier | Monomer Content of Protein Stock (%) | Reconstitution Profile (Appearance 0-5) | Monomer Content @ t = 0 (%) | Monomer Conservation (%) | MPL (% w/w) | Particle Size (×50) (μm) |
| PFCP1_46_1 | 99.59 | Appearance 0 | 99.09 | 99.5 | 34.53 | 5.15 |
| PFCP1_46_2 | 99.59 | Appearance 0 | 99.55 | 99.9 | 31.86 | 49.66 |

TABLE 31

| Results from Accelerated Stability Study | | | | | | |
|---|---|---|---|---|---|---|
| Sample Identifier | Monomer Content of Protein Stock (%) | Reconstitution Profile (0-5) or (NTU) | Monomer Content as % (weeks in storage) | % Monomer content conserved (weeks in storage) | MPL (% w/w) | % Change in Monomer Content over Time Period (%) |
| PFCP1_46_1 | 99.59 | Appearance 0 | 97.32 (13 weeks) | 97.6 | 35.94 | −2.27 |
| PFCP1_46_2 | 99.59 | Appearance 0 | 97.97 (13 weeks) | 98.0 | 36.57 | −1.63 |

These data demonstrate that, when precipitated under equivalent mixing regimes, particles incorporating precipitation protective additives, coprecipitated from propan-2-ol, are smaller than those coprecipitated from 2-methyl-1-propanol. Thus the size of particle can be advantageously tuned by choice of solvent or a mixture of solvents. Using propanantibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

The precipitations were carried out by addition, using a Rainin EDP3 pipette, of 2.5 mL volume of the aqueous mixture to 47.5 mL of solvent in a 125 mL vial, at 0.25 mL/second, whilst mixing rapidly with a 45 mm magnetic stirrer bar rotating at 1500 rpm. The concentrations of each of the components at the point of coprecipitation are given in Table 30. Following stirring for 60 seconds a 25 mL aliquot containing the precipitated particles were collected by filtration onto a 0.45 μM Millipore Durapore PVDF membrane and allowed to air dry, with no humidity control, at 22° C. (Room Temperature) for 16-24 hours.

The dry PCMC powder samples were there reconstituted back into PBS buffer at a target concentration of 1 mg/ml. The turbidity of the unfiltered reconstituted solutions was measured using a Hach Lange 2100AN turbidity meter, as described in Example 5. The protein loading of the particles was measured by determining the UV absorbance of the filtered reconstituted solution at 280 nm, using a ThermoScientific Biomate 5 ultra violet spectrophotometer. Changes in aggregation state of the antibody within the precipitated particles, as reconstituted solutions, were determined by comparing size exclusion chromatographs of the reconstituted material to the initial protein stock material, using a Waters Alliance 2690 Separations module using a 2487 dual wavelength detector as described in Example 5.

These data demonstrate that it is possible to combine different types of acidic and basic additives together to produce particles with high retention of protein integrity and excellent reconstitution profiles. Thus it is possible to combine basic amino acids with acidic sugars (e.g. PFCP1__88__4) and basic sugars with acidic amino acids (e.g. PFCP1__88__2) to produce particles in which an aggregation sensitive bioactive molecule is stabilized against changes in aggregation state. The highest level of stability was achieved for a formulation containing an acidic and basic additive combined with a neutral additive (PFCP1__88__5).

Example 15

Reconstitution of PCMC Formulations to Yield High Concentration Solutions

In this example the aggregation sensitive bioactive molecule used was a human monoclonal antibody, PfmAb, obtained from Pfizer Inc, Chesterfield, St Louis, Mo. This antibody is an $IgG_2$ isotype and binds to human cytotoxic T lymphocyte-associated antigen 4 (CTLA-4, CD152), supplied in 20 mM histidine buffer, 0.2 mg/ml Polysorbate 80.

TABLE 32

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PFCP1_88_1a | PfmAb (36) | Glycine (50) | L-Arginine (5.66) | L-Glutamic Acid (4.78) | — | Histidine & Polysorbate | 36.7 | Propan-2-ol |
| PFCP1_88_1b | PfmAb (36) | Glycine (50) | L-Arginine (5.66) | L-Glutamic Acid (4.78) | — | Histidine & Polysorbate | 36.7 | Propan-2-ol |
| PFCP1_88_2 | PfmAb (36) | Glycine (50) | N-Methyl-D-glucamine (6.34) | L-Glutamic Acid (4.78) | — | Histidine & Polysorbate | 36.45 | Propan-2-ol |
| PFCP1_88_3 | PfmAb (36) | Glycine (50) | D-Glucosamine HCl (7.01) | L-Glutamic Acid (4.78) | — | Histidine & Polysorbate | 36.20 | Propan-2-ol |

*Concentrations given are those in the final aqueous precipitation mixture. This mixture was mixed with solvent.

TABLE 33

Formulation Composition continued

| PFCP1_88_4 | PfmAb (36) | Glycine (50) | L-Arginine (5.66) | D-gluco-6-phosphate (9.17) | — | Histidine & Polysorbate | 35.13 | Propan-2-ol |
| PFCP1_88_5 | PfmAb (36) | Glycine (50) | N-Methyl-D-glucamine (6.34) | L-Glutamic Acid (4.78) | Myo-inositol (5.86) | Histidine & Polysorbate | 34.41 | Propan-2-ol |

*Concentrations given are those in the final aqueous precipitation mixture. This mixture was mixed with solvent.

TABLE 34

Results

| Sample Identifier | Monomer Content of Protein Stock (%) | Reconstitution Profile (NTU) | Monomer Content @ t = 0 (%) | Monomer Conservation (%) | MPL (% w/w) |
|---|---|---|---|---|---|
| PFCP1_88_1a | 99.53 | 2.88 | 97.32 | 97.78 | 35.71 |
| PFCP1_88_1b | 99.53 | 2.65 | 97.28 | 97.74 | 35.70 |
| PFCP1_88_2 | 99.53 | 2.50 | 97.62 | 98.08 | 44.83 |
| PFCP1_88_3 | 99.53 | 2.92 | 94.65 | 95.10 | 42.68 |
| PFCP1_88_4 | 99.53 | 2.40 | 97.92 | 98.38 | 42.22 |
| PFCP1_88_5 | 99.53 | 2.61 | 97.90 | 99.06 | 38.52 |

Two samples of antibody coated microcrystals, incorporating arginine and glutamic acid were prepared. The MPL and monomer content were measured as described in Example 4 and additionally the reconstitution time and turbidity was measured, when reconstituted at a significantly higher concentration of 72 mg/ml. A formulation without protein was also prepared to allow direct comparison of dissolution times.

The precipitations were carried out by addition, using a Rainin EDP3 pipette, of 2.5 mL volume of the aqueous mixture to 47.5 mL of solvent in a 125 mL vial, at approximately 0.25 mL/second, whilst mixing rapidly with a 45 mm magnetic stirrer bar rotating at 1500 rpm. The concentrations of each of the components at the point of coprecipitation are given in Table 32. Following stirring for 60 seconds the precipitated particles were collected by filtration onto a 0.45 µm Millipore Durapore PVDF membrane and allowed to air dry, with no humidity control, at approximately 22° C. (Room Temperature) for 16-24 hours.

The dry PCMC powder samples were then reconstituted back into PfmAb buffer at a target concentration of 72 mg/ml. The turbidity of the PfmAb protein stock as supplied and the unfiltered reconstituted solutions prepared at a target concentration of 72 mg/ml were measured using a Hach Lange 2100AN turbidity meter, as described in Example 5. The protein loading of the particles was measured by determining the UV absorbance of the diluted (1 mg/ml) then filtered reconstituted solution at 280 nm, using a ThermoScientific Biomate 5 ultra violet spectrophotometer. Changes in aggregation state of the antibody within the precipitated particles were determined by comparing size exclusion chromatographs of the diluted (1 mg/ml), reconstituted material to the initial protein stock material, using a Waters Alliance 2690 Separations module using a 2487 dual wavelength detector as as described in Example 5.

tively low turbidity values for such high concentrations. The concentration of antibody obtained in the reconstituted solution was approximately double that of the precipitation mixture showing that formation of PCMC can be advantageously used to concentrate proteins. Surprisingly, even when reconstituted at significantly higher target protein concentrations, the PCMC material was found to dissolve fairly rapidly. Sample PFCP1_96_2 required no mechanical agitation. The PCMC crystals readily dissolved on contact with the aqueous PfmAb buffer, in approximately 4 minutes, to produce an optically clear solution, with a turbidity value of 31.5 NTU. Sample PFCP1_96_3 was somewhat more hydrophobic in character, requiring some mechanical agitation to assist wetting of crystals, to yield an optically clear solution with a turbidity value of 34.8 NTU. In terms of monomer conservation, 95% and 99.9% of monomer was retained for propan-2-ol and 2-methyl-1-propanol respectively, which is consistent with previous observations in more dilute solutions. Sample PFCP1_96_1, which contained no protein, but only buffering components and the glycine crystalline coprecipitant, also dissolved rapidly to produce an optically clear solution in <2 minutes, as would be expected.

Example 16

Preparation of Human Serum Albumin Coated Glycine Microcrystals

Human serum albumin (A8763) was obtained from Sigma Aldrich and was dissolved in deionised water.

Two different samples were prepared:

1. Human serum albumin (HSA) coated glycine crystals [PTHSA_190_1]; prepared by precipitation of an aqueous mixture of HSA and glycine on addition to excess 2-methyl-1-propanol, and

TABLE 35

| | Formulation Composition | | | | | | | |
|---|---|---|---|---|---|---|---|---|
| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
| PFCP1_96_1 | — | Glycine (50) | — | — | — | Histidine & Polysorbate | 0 | Propan-2-ol |
| PFCP1_96_2 | PfmAb (36) | Glycine (50) | L-Arginine (11.3) | L-Glutamic Acid (9.56) | — | Histidine & Polysorbate | 33.17 | Propan-2-ol |
| PFCP1_96_3 | PfmAb (36) | Glycine (50) | L-Arginine (11.3) | L-Glutamic Acid (9.56) | — | Histidine & Polysorbate | 33.17 | 2-Methyl-1-Propanol |

*Concentrations given are those in the final aqueous precipitation mixture. This mixture was mixed with solvent.

TABLE 36

| | Results | | | | | | |
|---|---|---|---|---|---|---|---|
| Sample Identifier | Monomer Content of Protein Stock (%) | Turbidity of Protein Stock at 72 mg/ml (NTU) | Reconstitution Profile at target concentration of 72 mg/ml (NTU) | Dissolution Time (min) | Monomer Content @ t = 0 (%) | Monomer Conservation (%) | MPL (% w/w) |
| PFCP1_96_1 | — | — | Appearance 0 | 1.67 (No mechanical agitation required) | — | — | — |
| PFCP1_96_2 | 99.75 | 11.2 | 31.5 | <4 (No mechanical agitation required) | 94.77 | 95.0 | 28.9 |
| PFCP1_96_3 | 99.75 | 11.2 | 34.8 | 6 (Standing for 2 minutes; 4 minutes agitation on blood rotator @ 25 rpm. | 99.65 | 99.9 | 27.9 |

The data shows that PCMC, incorporating protective additive, can be reconstituted to produce high concentration protein solutions that retain high monomeric content and rela- 2. Human serum albumin coated glycine crystals [PTHSA_190_2]; incorporating protective additives prepared; by precipitation of an aqueous mixture of HSA, glycine, and basic protective additive, arginine, and the acidic protective additive, glutamic acid, on addition to excess 2-methyl-1-propanol.

The precipitations were carried out by addition, using a Rainin EDP3 pipette, of 1 mL volume of the aqueous mixture to 19 mL of solvent in a 30 mL vial, at approximately 0.25 mL/second, whilst mixing rapidly with a 25 mm magnetic stirrer bar rotating at 1500 rpm. The concentrations of each of the components in the aqueous mixture at the point of coprecipitation are given in Table 34. Following stirring for 60 seconds the precipitated particles were collected by filtration onto a 0.45 μm Millipore Durapore PVDF membrane and allowed to air dry, with no humidity control, at approximately 22° C. (Room Temperature) for 16-24 hours.

The dry PCMC powder samples were then reconstituted back into PBS buffer at a target concentration of 30 mg/ml. The turbidity of the unfiltered reconstituted solutions was measured using a Hach Lange 2100AN turbidity meter. The protein loading of the particles was measured by determining the UV absorbance of the filtered reconstituted solution at 280 nm, using a ThermoScientific Biomate 5 UV spectrophotometer. Changes in aggregation state of the antibody within the precipitated particles were determined by comparing size exclusion chromatographs of the reconstituted material with the initial protein stock material, using a Waters Alliance 2690 Separations module using a 2487 dual wavelength detector as detailed above in Table 4.

glycine crystals in the absence of buffer shows a decrease in the level of soluble monomeric species from 93.95% down to 87.98%. Dehydrated HAS coated onto glycine microcrystals and associated with precipitation protective additives, arginine and glutamic acid, shows no loss in the monomer content. (The slight increase in monomer content is probably due to experimental error in the integration of the chromatogram). These data demonstrate protective additives prevent changes in aggregation state with different types of aggregation sensitive bioactive molecules.

The invention claimed is:

1. A suspension of particles in a polar organic solvent comprising less than 25% water,
    wherein the particles comprise at least one bioactive molecule,
    wherein the particles have been prepared by precipitation of said bioactive molecule(s) from an aqueous composition comprising said bioactive molecule(s) and at least one cationic and at least one anionic precipitation stabilizing additives-, upon mixing with a greater than 3-fold excess of a polar organic solvent, wherein the resulting precipitated particles further comprise said precipitation stabilizing additive(s);
    wherein said bioactive molecule(s) is an aggregation-sensitive biomolecule(s); and

TABLE 37

Formulation Composition

| Sample Identifier | (a) Bioactive molecule (mg/ml) | (b) Co-precipitant (mg/ml) | (c) Basic Additive (mg/ml) | (d) Acidic Additive (mg/ml) | (e) Neutral Additive (mg/ml) | Residual Trace Excipients | TPL (% w/w) | Solvent |
|---|---|---|---|---|---|---|---|---|
| PTHSA_190_1 | HSA (75) | Glycine (75) | — | — | — | — | 50 | 2-methyl-1-propanol |
| PTHSA_190_2 | HSA (75) | Glycine (75) | L-Arginine (21.8) | L-Glutamic Acid (18.4) | — | — | 39.44 | 2-methyl-1-propanol |

*Concentrations given are those in the final aqueous precipitation mixture. This mixture was mixed with solvent.

TABLE 38

Results

| Sample Identifier | Monomer Content of Protein Stock (%) | Reconstitution Profile (Appearance 0-5)* | Monomer Content @ t = 0 (%) | Monomer Conservation (%) | MPL (% w/w) |
|---|---|---|---|---|---|
| PTHSA_190_1 | 93.95 | Appearance 0 (11.5 NTU) | 87.98 | 93.65 | 50.3 |
| PTHSA_190_2 | 93.95 | Appearance 0 (10.2 NTU) | 95.55 | 101.7 | 33.8 |

*Samples were reconstituted at a target concentration of 30 mg/ml for reconstitution profiles. Thereafter samples were diluted to 5 mg/ml for UV and HPSEC analysis.

These data show that for samples prepared with and without additives the measured protein loading (MPL) and the theoretical protein loading (TPL) are very similar, showing that substantially all of the solid material present within the aqueous mixture has precipitated into propan-2-ol to form particles. Thus the complete composition of the particles can be determined from the weights of each of the material present with the aqueous solution including the phosphate and salts.

The beneficial effects of the additives in reducing changes in the aggregation state of the HSA on exposure to the 2-methyl-1-propanol are clear. The dehydrated HSA coated onto wherein the percentage of said bioactive molecules exhibiting a changed aggregation state from the aggregation state present prior to precipitation of said particles is less than 5%.

2. The suspension according to claim 1 which is substantially free from any polymeric excipients.

3. The suspension according to claim 1 wherein the bioactive molecule is a protein with molecular mass greater than 10 kDa.

4. The suspension according to claim 1 wherein the bioactive molecule is present in the range 20%-85% w/w.

5. The suspension according to claim 1 wherein the bioactive molecule is an antibody, antibody fragment, or antibody conjugate.

6. The suspension of claim 5, wherein the antibody, antibody fragment, or antibody conjugate is a human antibody, a humanized antibody, or a fragment or conjugate of a human or humanized antibody.

7. The suspension of claim 1, wherein the aggregation-sensitive biomolecule(s) are is selected from the group consisting of granulocyte-colony stimulating factor (GCSF), stem cell factor, leptin, hematopoietic factors, non-human growth factors, antiobesity factors, trophic factors, anti-inflammatory factors, enzymes, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma, omega), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors, insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), erythropoietin, thrombopoietin, platelet-derived growth factor (PGDF), colony simulating growth factors (CSFs), bone morphogenetic protein (BMP), superoxide dismutase (SOD), urokinase, streptokinase, and kallikrein.

8. The suspension of claim 1, wherein the aggregation-sensitive biomolecule(s) are selected from the group consisting of AVASTIN® (bevacizumab), BEXXAR® (Tositumomab), CAMPATH® (Alemtuzumab), ERBITUX® (Cetuximab), HUMIRA® (Adalimumab), RAPTIVA® (efalizumab), REMICADE® (InfliximabREOPRO® (Abciximab), SIMULECT® (Basiliximab), SYNAGIS® (Palivizumab), XOLAIR® (Omalizumab), ZENAPAX® (Daclizumab), ZEVALIN® (Ibritumomab Tiuxetan), and MYLOTARG® (gemtuzamab ozogamicin).

9. The suspension of claim 1, wherein the aggregation-sensitive biomolecule(s) are selected from the group consisting of therapeutic or diagnostic proteins and peptides; therapeutic or diagnostic nucleic acids and derivatives thereof; carbohydrates; plasmids; viruses; viral-like particles; antigens; and combination thereof.

10. The suspension of claim 1, wherein the aggregation-sensitive biomolecules show turbidity readings of less than 20 Nephelometric Turbidity Units immediately following precipitation from a polar organic solvent.

11. The suspension of claim 1, wherein the polar organic solvent is selected from the group consisting of isopropanol, isobutanol, and mixtures thereof.

12. The suspension of claim 1, wherein the particles are isolated and dried to provide dry particles that may be reconstituted in aqueous solvent to produce solutions in which the percentage of bioactive molecules exhibiting a changed aggregation state from the aggregation state present prior to precipitation of said particles is less than 5%.

13. The suspension according to claim 1, wherein the particles retain at least 95% of the bioactive molecule content following precipitation.

14. The suspension according to claim 13 wherein the particles retain at least 95% of the bioactive molecule content following storage in a sealed vial at 40° C. for at least 13 weeks.

15. The suspension according to claim 1 wherein the particles have a median diameter of less than 100 µm.

16. The suspension according to claim 15 wherein the particles have a median diameter of less than 10 µm.

17. The suspension of claim 1, wherein the at least one anionic precipitation stabilizing additive(s) is selected from the group consisting of amino acids with an acidic side chain, N-protected amino acids with polar non-ionizable side chains, polyol acids, and sugar acids.

18. The suspension of claim 1, wherein the at least one cationic precipitation stabilising additive(s) is selected from the group consisting of amino acids with a basic side chain, C-protected amino-acids with polar non-ionizable side chains, amino polyols and amino sugars.

19. The suspension of claim 1, wherein the cationic precipitation stabilising additive is a basic precipitation stabilising additive.

20. The suspension according to claim 19 wherein the at least one basic precipitation stabilising additive(s) is selected from: amino acids with a basic side chain, C-protected amino-acids with polar non-ionisable side chains, amino polyols and amino sugars.

21. The suspension 20 wherein the basic additive is at a concentration of 1 mg/ml to 35 mg/ml in the aqueous composition.

22. The suspension according to claim 1 further comprising a neutral non-polymeric additive selected from: neutral amino acids with polar non-ionisable side chains, polyols, sugars, disaccharides and trisaccharides.

23. The suspension of claim 22, wherein the neutral precipitation stabilizing additive(s) is selected from the group consisting of polyols, monosaccharides, disaccharides and trisaccharides.

24. The suspension according to claim 22 wherein the neutral additive is at a concentration of 1 mg/ml to 50 mg/ml of the aqueous composition.

25. The suspension according to claim 1 wherein the aqueous composition further comprises a core forming coprecipitant.

26. The suspension according to claim 25 wherein the coprecipitant is present in the aqueous composition at a concentration less than its solubility limit and in the range 5 mg/ml to 200 mg/ml.

27. The suspension according to claim 25 wherein the coprecipitant has a pH in the pH range of 4-9.

28. The suspension according to claim 27 wherein the coprecipitant is alanine, asparagine, glutamine, glycine, histidine, mannitol, myoinositol, taurine, trehalose or valine.

29. The suspension according to claim 25 wherein the bioactive molecule is present in the range 0.1% w/w to 50% w/w.

30. The suspension according to claim 29, wherein the particles comprise a core made from the coprecipitant coated with the bioactive molecule and the anionic and cationic precipitation stabilizing additives.

* * * * *